(12) United States Patent
Gates et al.

(10) Patent No.: US 11,034,996 B2
(45) Date of Patent: Jun. 15, 2021

(54) NUCLEIC ACID SEQUENCE AND CAPTURE BY FORMATION OF AN ABASIC SITE-DERIVED CROSS-LINK

(71) Applicant: The Curators of the University of Missouri, Columbia, MO (US)

(72) Inventors: Kent Gates, Columbia, MO (US); Li-Qun Gu, Columbia, MO (US); Maryam Imani Nejad, Columbia, MO (US); Ruicheng Shi, Columbia, MO (US); Xinyue Zhang, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 56 days.

(21) Appl. No.: 16/289,199

(22) Filed: Feb. 28, 2019

(65) Prior Publication Data
US 2019/0271029 A1 Sep. 5, 2019

Related U.S. Application Data

(60) Provisional application No. 62/637,476, filed on Mar. 2, 2018.

(51) Int. Cl.
*C12Q 1/6827* (2018.01)
*C12Q 1/6806* (2018.01)
*C12Q 1/6886* (2018.01)

(52) U.S. Cl.
CPC ......... *C12Q 1/6827* (2013.01); *C12Q 1/6806* (2013.01); *C12Q 1/6886* (2013.01); *C12Q 2600/156* (2013.01)

(58) Field of Classification Search
CPC .. C12Q 1/6827; C12Q 1/6806; C12Q 1/6886; C12Q 2600/156; C12Q 1/6825
See application file for complete search history.

(56) References Cited

U.S. PATENT DOCUMENTS

| 9,395,353 B2 | 7/2016 | Gu et al. |
| 9,574,228 B2 | 2/2017 | Gu et al. |
| 9,732,379 B2 | 8/2017 | Gu et al. |

FOREIGN PATENT DOCUMENTS

| WO | 2012/009578 A2 | 1/2012 |
| WO | 2014/144217 A1 | 9/2014 |

OTHER PUBLICATIONS

Begum et al. Modern Pathology. 2004. 17:1359-1363. (Year: 2004).*
(Continued)

*Primary Examiner* — Joseph G. Dauner
(74) *Attorney, Agent, or Firm* — Thompson Coburn LLP; William A. Holtz

(57) ABSTRACT

Disclosed herein is a method of covalently crosslinking DNA strands. In certain aspects, the method comprises incubating a hybridized, double-stranded DNA polynucleotide (dsDNA), comprising a probe strand that comprises an abasic (Ap) residue and an at least partially complementary target strand that comprises a 2'-deoxyadenosine (dA) residue, wherein incubation occurs under conditions that allow for a covalent crosslinking reaction to occur between the Ap residue in the probe strand and the dA residue in the target strand.

14 Claims, 19 Drawing Sheets

Figure 1A:
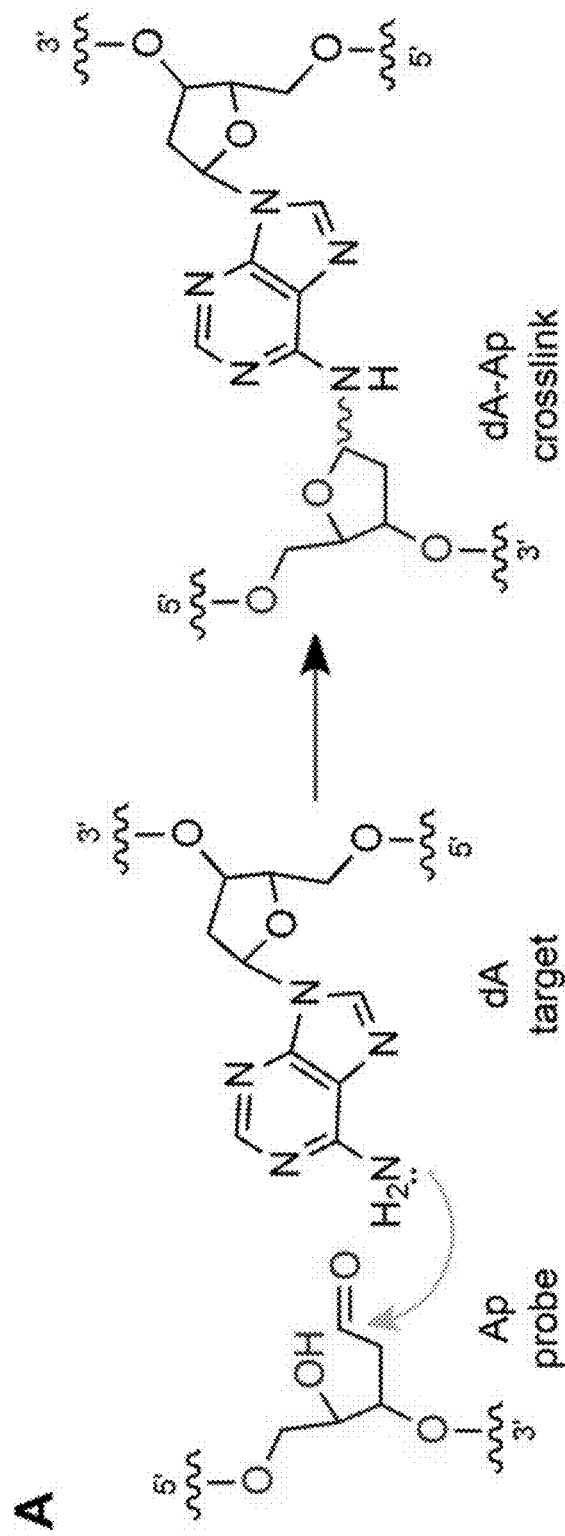

Specification includes a Sequence Listing.

(56) References Cited

OTHER PUBLICATIONS

Aksimentiev et al., "Imaging a-Hemolysin with Molecular Dynamics: Ionic Conductance, Osmotic Permeability, and the Electrostatic Potential Map", Biophysical Journal, 2005, pp. 3745-3761, vol. 88.
Ang et al., "Rapid and Label-Free Single-Nucleotide Discrimination via an Integrative Nanoparticle—Nanopore Approach", ACS Nano, 2012, pp. 8815-8823, vol. 6, No. 10.
Bollag et al., "Vemurafenib: The First Drug Approved for BRAF-Mutant Cancer", Nature Reviews, 2012, pp. 873-886, vol. 11.
Catalano et al., "Chemical Structure and Properties of Interstrand Cross-Links Formed by Reaction of Guanine Residues with Abasic Sites in Duplex DNA", Journal of American Chemical Society, 2015, pp. 3933-3945, vol. 137.
Catalano et al., "Effective Molarity in a Nucleic Acid-Controlled Reaction", Bioorganic and Medicinal Chemistry Letters, 2016, pp. 2627-2630, vol. 26.
Coleman et al., "Covalent Cross-Linking of Duplex DNA Using 4-thio-2'-deoxyuridine as a Readily Modifiable Platform for Introduction of Reactive Functionality into Oligonucleotides", Nucleic Acids Research, 1997, pp. 4771-4777, vol. 25, No. 23.
Costes et al., "Psoralen-Modified Oligonucleotide Primers Improve Detection of Mutations by Denaturing Gradient Gel Electrophoresis and Provide an Alternative to GC-Clamping", Human Molecular Genetics, 1993, pp. 393-397, vol. 2, No. 4.
Demidov et al., "Two Sides of the Coin: Affinity and Specificity of Nucleic Acid Interactions", Trends in Biochemical Sciences, 2004, pp. 62-71, vol. 24, No. 2.
Dutta et al., "Interstrand Cross-Links Generated by Abasic Sites in Duplex DNA", Journal of American Chemical Society, 2007, pp. 1852-1853, vol. 129.
French et al., "Detection of the Factor V Leiden Mutation by a Modified Photo-Cross-Linking Oligonucleotide Hybridization Assay", Clinical Chemistry, 2004, pp. 296-305, vol. 50, No. 2.
Fujimoto et al., "Details of the Ultrafast DNA Photo-Cross-Linking Reaction of 3-Cyanovinylcarbazole Nucleoside: Cis—Trans Isomeric Effect and the Application for SNP-Based Genotyping", Journal of the American Chemical Society, 2013, pp. 16161-16167, vol. 135.
Giacomini et al., "The Pharmacogenetics Research Network: From SNP Discovery to Clinical Drug Response", Nature, 2007, pp. 328-345, vol. 81, No. 3.
Gibbs et al., "Novel Mutagenic Properties of Abasic Sites in *Saccharomyces cerevisiae*", Journal of Molecular Biology, 1995, pp. 229-236, vol. 251.
Hattori et al., "Formation of Highly Selective and Efficient Intersrand Cross-Linking to Thymine Without Photo-Irradiation", Chem. Commun., 2009, pp. 6463-6465.
Howorka et al., "Kinetics of Duplex Formation for Individual DNA Strands Within a Single Protein Nanopore", PNAS, 2001, pp. 12996-13001, vol. 98, No. 23.
Hu et al., "Fluorescence in Situ Hybridization (FISH): An Increasingly Demanded Tool for Biomarker Research and Personalized Medicine", 2014, Biomarker Research, 13 pages, vol. 2, No. 3.
Iqbal et al., "Solid-State Nanopore Channels with DNA Selectivity", Nature, 2007, pp. 243-248, vol. 2.
Johnson et al., "Dynamics of a DNA Mismatch Site Held in Confinement Discriminate Epigenetic Modifications of Cytosine", Journal of the American Chemical Society, 2017, pp. 2750-2756, vol. 139.
Johnson et al., "On the Formation and Properties of Interstrand DNA—DNA Cross-Links Forged by Reaction of an Abasic Site with the Opposing Guanine Residue of 5'-CAp Sequences in Duplex DNA", Journal of the American Chemical Society, 2013, pp. 1051-1025, vol. 135.
Katsanis et al., "Molecular Genetic Testing and the Future of Clinical Genomics", Nature Reviews, 2013, pp. 415-423, vol. 14.
Knez et al., "Emerging Technologies for Hybridization Based Single Nucleotide Polymorphism Detection", Analyst, 2014, pp. 353-370, vol. 139.
Kong et al., "Single Molecule Based SNP Detection using Designed DNA Carriers and Solid-State Nanopores", Chem. Commun., 2017, pp. 436-439, vol. 53.
Lander, "Initial Impact of the Sequencing of the Human Genome", Nature, 2011, pp. 187-197, vol. 470.
Lapitan et al., "Nano-Enabled Bioanalytical Approaches to Ultrasensitive Detection of Low Abundance Single Nucleotide Polymorphisms", Analyst, 2015, pp. 3872-3887, vol. 140.
Li et al., "Electrochemical Detection of Single-Nucleotide Mismatches using an Electrode Microarray", Analytical Chemistry, 2006, pp. 6096-6101, vol. 78.
Lindahl et al., "DNA N-Glycosidases Properties of Uracil-DNA Glycosidase from *Escherichia coli*", The Journal of Biological Chemistry, 1977, pp. 3286-3294, vol. 252, No. 10.
Luce et al., "Chemical Cross-Linking of Drugs to DNA", Methods in Enzymology, 2001, pp. 396-412, vol. 340.
Maglia et al., "Enhanced Translocation of Single DNA Molecules Through a-Hemolysin Nanopores by Manipulation of Internal Charge", PNAS, 2008, pp. 19720-19725, vol. 105, No. 50.
Maxam et al., "Sequencing End-Labeled DNA with Base-Specific Chemical Cleavages", Methods in Enzymology, 1980, pp. 499-560, vol. 65, No. 1.
McCarthy et al., "Genomic Medicine: A Decade of Successes, Challenges, and Opportunities", Science Translational Medicine, 2013, pp. 18 pages, vol. 5, No. 189.
Nakane et al., "A Nanosensor for Transmembrane Capture and Identification of Single Nucleic Acid Molecules", Biophysical Journal, 2004, pp. 615-621, vol. 87.
Nejad et al., "Sequence-Specific Covalent Capture Coupled with High-Contrast Nanopore Detection of a Disease-Derived Nucleic Acid Sequence", ChemBioChem, 2017, pp. 1383-1386, vol. 18.
Nishimoto et al., "4-Vinyl-Substituted Pyrimidine Nucleosides Exhibit the Efficient and Selective Formation of Interstrand Cross-Links with RNA and Duplex DNA", Nucleic Acids Research, 2013, vol. 41, No. 13.
Peng et al., "Facile SNP Detection Using Bifunctional, Cross-Linking Oligonucleotide Probes", Nucleic Acids Research, 2008, pp. 7 pages, vol. 36, No. 5.
Price et al., "Chemical and Structural Characterization of Interstrand Cross-Links Formed Between Abasic Sites and Adenine Residues in Duplex DNA", Nucleic Acids Research, 2015, pp. 3434-3441, vol. 43, No. 7.
Price et al., "Interstrand DNA-DNA Cross-Link Formation Between Adenine Residues and Abasic Sites in Duplex DNA", Journal of the American Chemical Society, 2014, pp. 3483-3490, vol. 136.
Rossetti et al., "The Structural Impact of DNA Mismatches", Nucleic Acids Research, 2015, pp. 4309-4321, vol. 43, No. 8.
Rubinstein et al., "Incidence of the V600K Mutation Among Melanoma Patients with BRAF Mutations, and Potential Therapeutic Response to the Specific BRAF Inhibitor PLX4032", Journal of Translational Medicine, 2010, 3 pages, vol. 8, No. 67.
Sanchez-Quesada et al., "Single DNA Rotaxanes of a Transmembrane Pore Protein", Angew. Chem. Int. Ed. Engl., 2004, pp. 3063-3067, vol. 43.
Sczepanski et al., "Scope and Mechanism of Interstrand Cross-Link Formation by the C4'-Oxidized Abasic Site", Journal of American Chemical Society, 2009, pp. 11132-11139, vol. 131.
Shen et al., "Genotyping and Quantification Techniques for Single-Nucleotide Polymorphisms", Trends in Analytical Chemistry, 2015, pp. 1-13, vol. 69.
Shi et al., "Nanopore Sensing", Analytical Chemistry, 2017, pp. 157-188, vol. 89.
Silverman et al., "Detecting RNA and DNA with Templated Chemical Reactions", Chem. Rev., 2006, pp. 3775-3789, vol. 106.
Silverman et al., "Oligonucleotide Proves for RNA-Targeted Fluorescence in situ Hybridization", Advances in Clinical Chemistry, 2007, pp. 79-115, vol. 43.
Song et al., "Structure of Staphylococcal a-Hemolysin, a Heptameric Transmembrane Pore", Science, 1996, pp. 1859-1866, vol. 274, No. 5294.

(56) References Cited

OTHER PUBLICATIONS

Stevens et al., "Furan-Modified Oligonucleotides for Fast, High-Yielding and Site-Selective DNA Inter-Strand Cross-Linking with Non-Modified Comlements", Nucleic Acids Research, 2009, pp. 1555-1565, vol. 37, No. 5.
Sun et al., "Reversible and Adaptive Resistance to BRAF(V600E) Inhibition in Melanoma", Nature, 2014, 13 pages, vol. 508.
Tian et al., "Interference-Free Detection of Genetic Biomarkers Using Synthetic Dipole-Facilitated Nanopore Dielectrophoresis", ACS Nano, 2017, pp. 1204-1213, vol. 11.
Tyagi et al., "Molecular Beacons: Probes that Fluoresce Upon Hybridization", Nature, 1996, pp. 303-308, vol. 14.
Varela et al., "A Simple, High-Yield Synthesis of DNA Duplexes Containing a Covalent, Thermally Cleavable Interstrand Cross-Link at a Defined Location", Angew. Chem., 2015, pp. 7776-7779, vol. 127.
Varshney et al., "Specificities and Kinetics of Uracil Excision from Uracil-Containing DNA Oligomers by *Escherichia coli* Uracil DNA Glycosylase", Biochemistry, 1991, pp. 4055-4061, vol. 30.
Venkatesan et al., "Nanopore Sensors for Nucleic Acid Analysis", Nature Nanotechnology, 2011, pp. 615-624, vol. 6.
Vieregg et al., "Selective Nucleic Acid Capture with Shielded Covalent Probes", Journal of the American Chemical Society, 2013, pp. 9691-9699, vol. 135.
Wang et al., "Nanopore-Based Detection of Circulating MicroRNAs in Lung Cancer Patients", National Nanotechnology, 2012, pp. 668-674, vol. 6, No. 10.
Wanunu et al., "Nanopores: A Journey Towards DNA Sequencing", Phys. Life. Rev., 2012, pp. 125-158, vol. 9, No. 2.
Wetmur, "DNA Probes: Applications of the Principles of Nucleic Acid Hybridization", Critical Reviews in Biochemistry and Molecular Biology, 1991, pp. 227-259, vol. 26, No. 3.
Yang et al., "Characterization of Interstrand DNA-DNA Cross-Links Derived from Abasic Sites Using Bacteriophage 29 DNA Polymerase", Biochemistry, 2015, pp. 4259-4266, vol. 54.
Zhang et al., "Characterization of Interstrand DNA-DNA Cross-Links Using the a-Hemolysin Protein Nanopore", ACS Nano, 2015, pp. 11812-11819, vol. 9, No. 12.
Zhang et al., "Mimicking Ribosomal Unfolding of RNA Pseudoknot in a Protein Channel", Journal of the American Chemical Society, 2015, pp. 15742-15752, vol. 137.
Zhao et al., "Detecting SNPs Using a Synthetic Nanopore", Nano Letters, 2007, pp. 1680-1685, vol. 7, No. 6.

\* cited by examiner

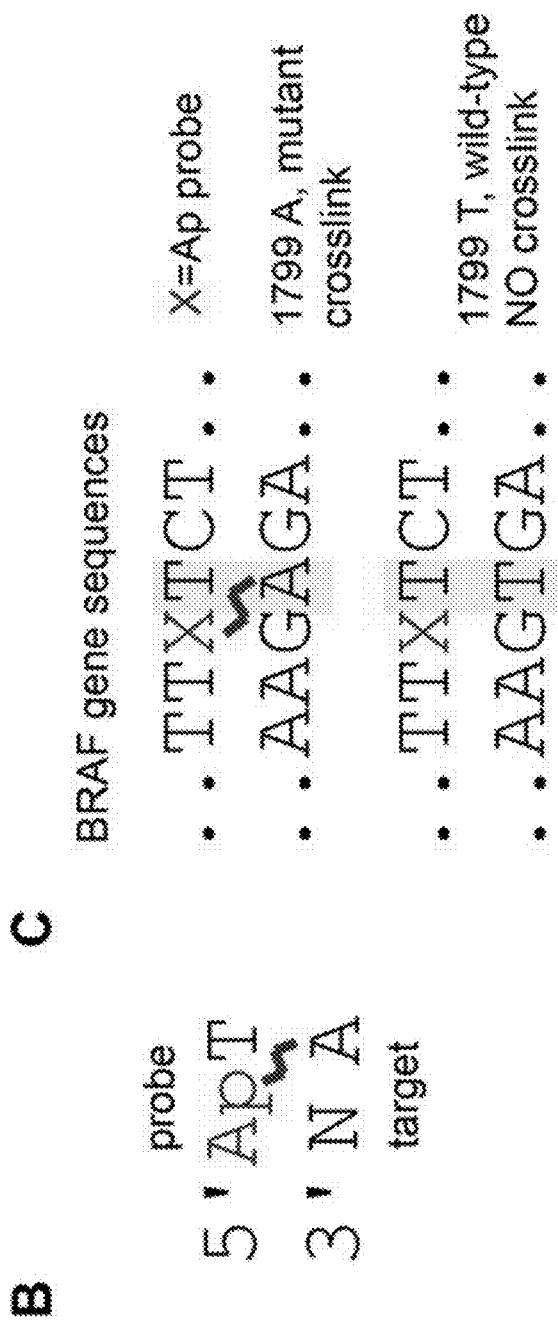
Figure 1B,C

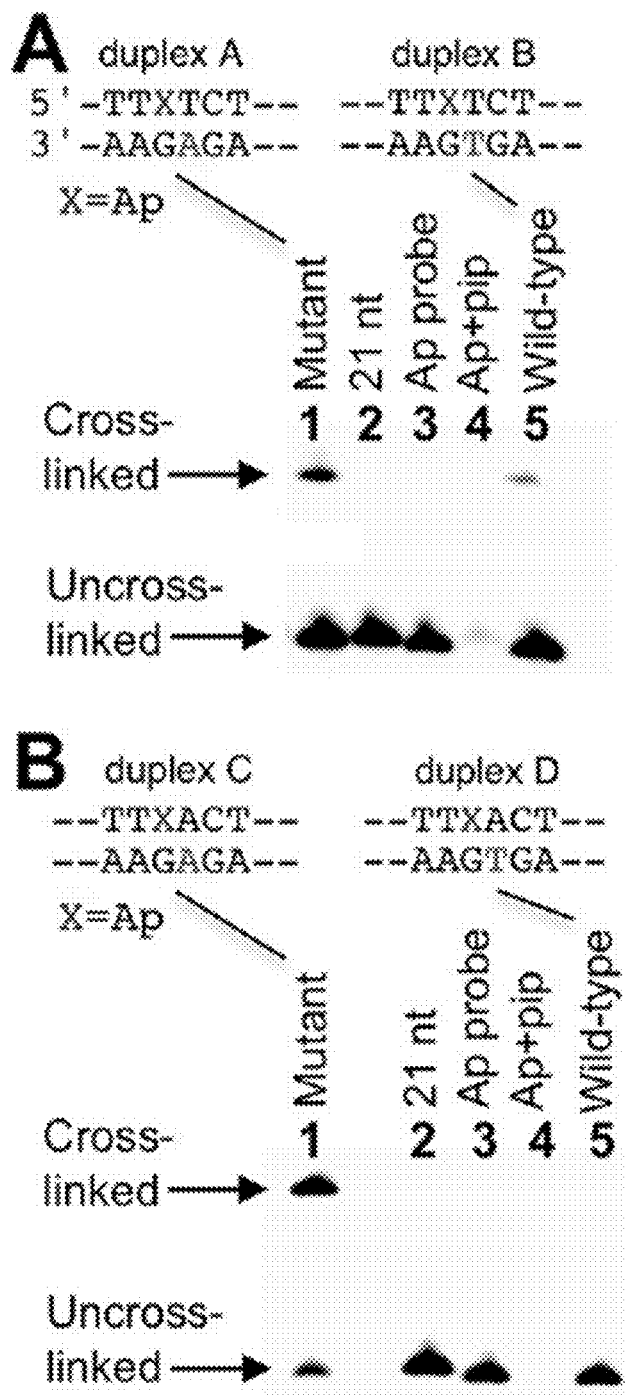
Figure 2A,B

A  5'-ATCGAGATTTXTCTGTAGCTA ← Probe
   3'-TAGCTCTAAAGAGACATCGAT ← Target

B  5'-ATCGAGATTTXTCTGTAGCTA
   3'-TAGCTCTAAAGTGACATCGAT

C  5'-ATCGAGATTTXACTGTAGCTA
   3'-TAGCTCTAAAGAGACATCGAT

D  5'-ATCGAGATTTXACTGTAGCTA
   3'-TAGCTCTAAAGTGACATCGAT

E  5'-ATCGAGATTTXACTGTAGCTAC30
   3'-TAGCTCTAAAGAGACATCGAT

F  5'-ATCGAGATTTXACTGTAGCTAC30

G  3'-TAGCTCTAAAGAGACATCGAT

X = Ap, Top strands 5'-$^{32}$P-labeled

Figure 7

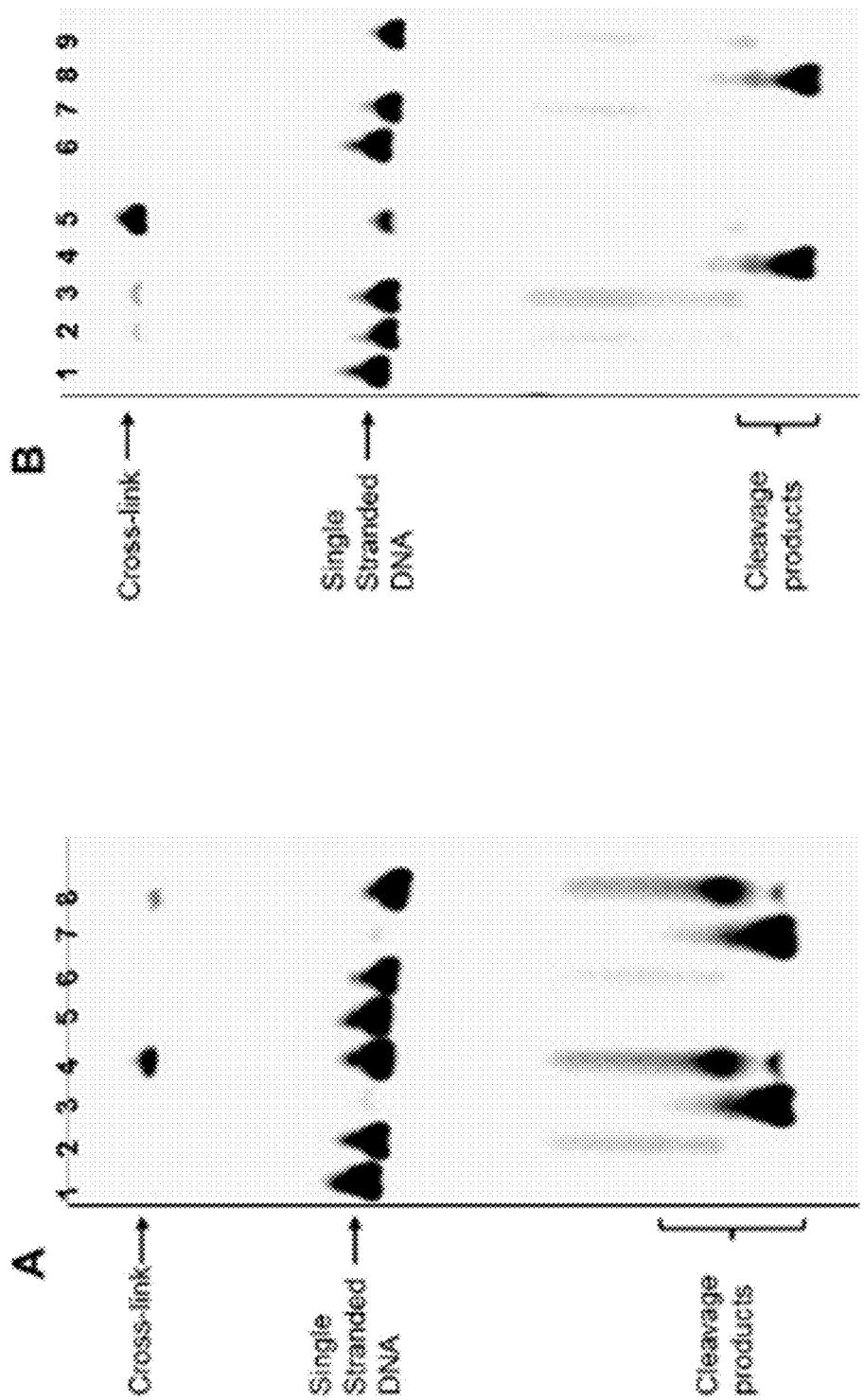
Figure 8A,B

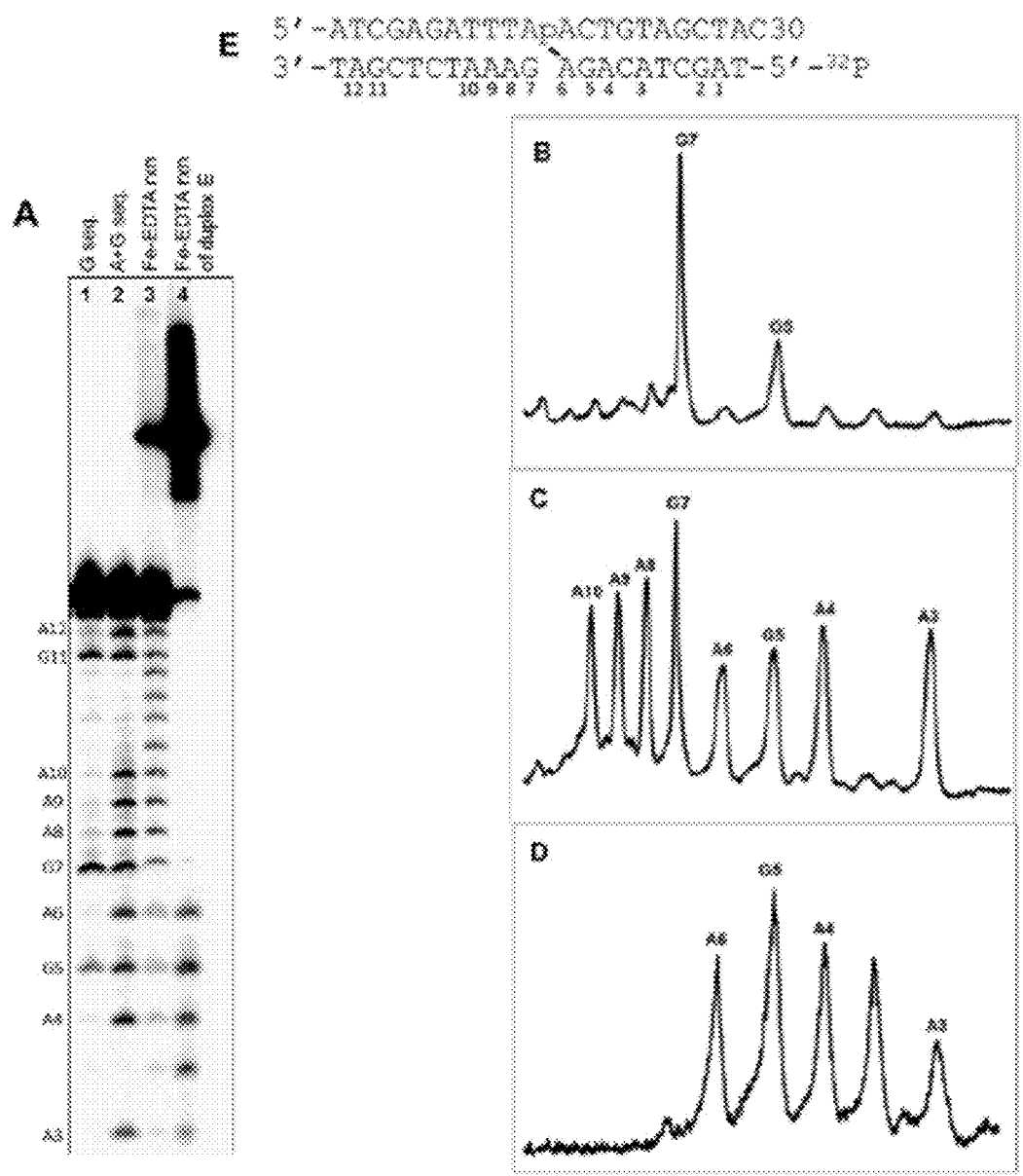
Figure 9A-E

SEQUENCE LISTING

<160> NUMBER OF SEQ ID NOS: 5

<210> SEQ ID NO 1
<211> LENGTH: 50
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: abasic residue (Ap)

<400> SEQUENCE: 1
atcgagattt actgtagcta cccccccccc cccccccccc cccccccccc                50

<210> SEQ ID NO 2
<211> LENGTH: 21
<212> TYPE: DNA
<213> ORGANISM: Homo sapiens

<400> SEQUENCE: 2
tagctctaaa gagacatcga t                                               21

<210> SEQ ID NO 3
<211> LENGTH: 21

```
<212> TYPE: DNA
<213> ORGANISM: Homo sapiens

<400> SEQUENCE: 3
tagctctaaa gtgacatcga t                                              21

<210> SEQ ID NO 4
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: abasic residue (Ap)

<400> SEQUENCE: 4
atcgagattt tctgtagcta                                                20

<210> SEQ ID NO 5
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(11)
<223> OTHER INFORMATION: abasic residue (Ap)

<400> SEQUENCE: 5
atcgagattt actgtagcta                                                20
```

NUCLEIC ACID SEQUENCE AND CAPTURE BY FORMATION OF AN ABASIC SITE-DERIVED CROSS-LINK

CROSS-REFERENCE TO RELATED APPLICATIONS

This is a U.S. Non-Provisional application which claims the benefit of U.S. Provisional Application Ser. No. 62/637,476, filed Mar. 2, 2018, which is incorporated herein by reference in its entirety.

STATEMENT REGARDING FEDERALLY-SPONSORED RESEARCH AND DEVELOPMENT

This invention was made with government support under R01 ES021007 and R01 GM114204 both awarded by the National Institutes of Health (NIH). The government has certain rights in the invention.

REFERENCE TO SEQUENCE LISTING SUBMITTED ELECTRONICALLY

The content of the electronically submitted sequence listing in the ASCII text file (Name: UMC 181704 Substitute Seq List ST25.txt; Size: 1424 4 bytes; and Date of Creation: Apr. 24, 2019) filed with the application is incorporated herein by reference in its entirety.

BACKGROUND

Methods for the detection of DNA and RNA sequences are important in research and medicine (E. S. Lander, *Nature* 2011, 470, 187; J. J. McCarthy, et al., *Sci. Transl. Med.* 2013, 5, 189sr4; P. E. M. Gibbs, C. W. Lawrence, *J. Mol. Biol.* 1995, 251, 229; K. M. Giacomini, et al., *Clin. Pharmacol. Ther.* 2007, 81, 328). Many strategies for the detection of nucleic acid sequences rely on Watson-Crick hybridization of a probe strand to target DNA or RNA in samples (A. P. Silverman, et al., *Chem. Rev.* 2006, 106, 3775; J. G. Wetmur, *Crit. Rev. Biochem. Mol. Biol.*, 1991, 26, 227; S. Tyagi, et al., *Nat. Biotechnol.* 1996, 14, 303; A. P. Silverman, et al., *Adv. Clin. Chem.* 2007, 43, 79; V. V. Demidov, et al., *Trends Biochem. Sci.* 2004, 29, 62; L. Hu, et al., *Biomark. Res.* 2014, 2, 3). The noncovalent, inherently reversible nature of nucleic acid hybridization presents challenges, however, because the signal can be compromised by partial denaturation of the probe-target duplex during analysis (i.e., washing). The use of longer (>20 nt) probes increases the stability of probe-target complexes but degrades sequence specificity (Id.).

Covalent crosslinks can be used to stabilize target-probe complexes (B. Costes, et al., *Human Mol. Genet.* 1993, 2, 393; C. French, et al., *Clin. Chem.* 2004, 50, 296; J. R. Vieregg, et al., *J. Am. Chem. Soc.* 2013, 135, 9691) and, in some cases, can provide an additional layer of target selectivity beyond that afforded by Watson-Crick hybridization (X. Peng, et al., *Nucleic Acids Res.* 2008, 36, e31; K. Stevens, et al., *Nucleic Acids Res.* 2009, 37, 1555; A. Nishimoto, et al., *Nucleic Acids Res.* 2013, 41, 6774; K. Hattori, et al., *Chem. Commun.* 2009, 6463-6465; R. S. Coleman, et al., *Nucleic Acids Res.* 1997, 25, 4771; K. Fujimoto, et al., *J. Am. Chem. Soc.* 2013, 135, 16161). There remains a need, however, for new crosslinking reactions that might be useful for the covalent capture of specific nucleic acid sequences.

SUMMARY

The present disclosure is drawn to methods of covalently crosslinking nucleic acid strands. In certain aspects, the method comprises incubating a hybridized, double-stranded nucleic acid molecule that comprises (i) a probe strand that comprises an abasic (Ap) residue and (ii) an at least partially complementary target strand that comprises a 2'-deoxyadenosine (dA) residue. In certain aspects, the incubation occurs under conditions that allow for a covalent crosslinking reaction to occur between the Ap residue in the probe strand and the dA residue in the target strand. In certain aspects, the Ap residue is at a position immediately 5' adjacent to the nucleotide residue in the probe strand that is directly opposite of the dA residue in the target strand. In certain aspects, the probe strand, the target strand, or both the probe strand and the target strand, is/are a DNA molecule(s). In certain aspects, the nucleotide residue in the probe strand that is directly opposite of the dA residue in the target strand is 2'-deoxyadenosine (dA).

In certain aspects of the methods disclosed herein, the probe strand can be less than or can be less than about, can be or can be about, or can be between any or can be between any of about 100, 90, 80, 70, 60, 50, 40, 30, 29, 28, 27, 26, 25, 24, 23, 22, 21, 20, 19, 18, 17, 16, 15, 14, 13, or 12 nucleotides in length.

In certain aspects of the methods disclosed herein, the target strand can be at least or can be at least about, can be or can be about, or can be between any or can be between any of about 12, 13, 14, 15, 16, 17, 18, 19, 20, 21, 22, 23, 24, 25, 26, 27, 28, 29, 30, 40, 50, 60, 70, 80, 90, or 100 nucleotides in length.

In certain aspects of the methods disclosed herein, the hybridized nucleic acid molecule can comprise a hybridized portion containing the Ap residue of the probe strand that can be at least or can be at least about, can be or can be about, or can be between any or can be any of about, 12, 13, 14, 15, 16, 17, 18, 19, 20, 21, 22, 23, 24, 25, 26, 27, 28, 29, 30, 40, 50, 60, 70, 80, 90, or 100 contiguous nucleotides in length.

In certain aspects of the methods disclosed herein, the hybridized portion containing the Ap residue of the probe strand can be at least or can be at least about, can be or can be about, or can be between any or can be between any of about 50%, 60%, 70%, 75%, 80%, 85%, 90%, 95%, 96%, 97%, 98%, or 99% complementary, or can be 100% complementary, excluding the position of the Ap residue.

In certain aspects of the methods disclosed herein, the crosslinking can increase stability of the double-stranded nucleic acid molecule in comparison to a hybridized nucleic acid molecule with identical probe strand and target strand sequences not being crosslinked.

The present disclosure also provides for methods of detecting the presence or absence of a dA residue at a particular position in a DNA target strand. In certain aspects, the method comprises incubating a hybridized double-stranded DNA molecule (dsDNA) that comprises (i) a probe strand that comprises an abasic (Ap) residue and (ii) an at least partially complementary target strand. In certain aspects, the Ap residue of the probe strand is at a position that is immediately 5' adjacent to the nucleotide residue in the probe strand that is directly opposite to the particular position in the target strand where the presence or absence of the dA residue is to be detected. In certain aspects, the incubation occurs under conditions that allow for a covalent crosslinking reaction to occur between the Ap residue in the probe strand and the dA residue in the target strand, if present. In certain aspects, a dA residue is present at the particular position in the target strand and a covalent crosslinking reaction occurs between the Ap residue in the probe strand and the dA residue in the target strand. In certain aspects, the method detects the presence of the dA residue in the target strand. In certain aspects, covalently crosslinking of the probe strand and the target strand is detected by gel electrophoresis, monitoring of thermal stability, fluorescence methods (i.e. FRET), electrochemistry, surface plasmon resonance, or a nanopore-based sensor. In certain aspects, covalently crosslinking of the probe strand and the target strand is detected by a nanopore-based sensor.

The present disclosure also provides for methods of detecting a mutation in a wild-type sequence. In certain aspects of the methods disclosed herein, the method comprises detecting the presence or absence of a dA residue at a particular position in a target strand according to any of the methods disclosed herein. In certain aspects, the dA residue is present at the particular position in the target strand and the mutation comprises a T→A, C→A, or G→A mutation or the dA residue is absent at the particular position in the target strand and the mutation comprises an A→T, A→C, or A→G mutation. In certain aspects, the mutation comprises a T→A, C→A, or G→A mutation and the nucleotide residue in the probe strand that is at the position immediately 5' adjacent to the Ap residue in the probe strand is complementary to the wild-type sequence of the target strand. In certain aspects, the presence or absence of the dA residue represents a disease relevant mutation, such as a mutation that causes or is correlated with cancer.

The present disclosure also provides for methods of identifying a bacterial, viral, or fungal species, subspecies, or strain. In certain aspects, the method comprises detecting the presence or absence of a dA residue at a particular position in a target strand according to the method of any of the methods disclosed herein. In certain aspects, the target strand is obtained from a sample taken from a bacteria, virus, or fungus. In certain aspects, the presence or absence of the dA in the target strand is used to identify the species, subspecies, or strain.

The present disclosure also provides for isolated covalently crosslinked, double-stranded nucleic acid molecules, which, in certain aspects comprise a probe strand that comprises an abasic (Ap) residue and a target strand that comprises a 2'-deoxyadenosine (dA) residue. In certain aspects, the Ap residue is at a position immediately 5' adjacent to the nucleotide residue in the probe strand that is directly opposite to the dA residue in the target strand. In certain aspects, the Ap residue is covalently crosslinked to the dA residue in the target strand that is directly opposite to the nucleotide residue in the probe strand that is immediately 3' adjacent to the Ap residue. In certain aspects, the probe strand, the target strand, or both the probe strand and the target strand, is/are DNA molecule(s). In certain aspects, the nucleotide residue in the probe strand that is immediately 3' adjacent to the Ap residue is A.

In certain aspects, the probe strand and/or the target strand comprises a terminal extension that is covalently attached to the 5' end, the 3' end, or both the 5' end and the 3' end of the strand. In certain aspects, the terminal extension is covalently attached to the 3' end of the strand and is selected from the group consisting of poly(dC)$_{(3-33)}$, poly(dG)$_{(3-33)}$, poly(dA)$_{(3-33)}$, poly(dT)$_{(3-33)}$, and poly(dN)$_{(3-33)}$, where N is any combination of 2'-deoxycytosine, 2'-deoxyguanosine, 2'-deoxyadenosine, thymine, an abase, inosine, xanthosine, 7-methylguanosine, dihydrouridine, or 5-methylcytidine.

BRIEF DESCRIPTION OF THE DRAWINGS/FIGURES

FIG. 1A-C. FIG. 1 shows the covalent capture of specific nucleic acid sequences by interstrand crosslink formation: A) covalent crosslink formation by reaction of an Ap aldehyde residue in the probe strand with an adenine residue in the target sequence; B) sequence motif for dA-Ap crosslinking reaction; and C) sequence-specific covalent capture of the mutant BRAF gene sequence by an Ap-containing probe strand.

FIG. 2A,B. FIG. 2 shows Ap-containing probes selectively crosslink with the 1799 T→A mutant BRAF kinase gene sequence: A) gel electrophoretic analysis of crosslink formation in 21 bp duplexes containing an Ap-containing probe and either the mutant (lane 1) or wild-type (lane 5) BRAF sequence and B) crosslinking by an Ap probe containing an adenine residue on the 3'-side of the Ap site is completely selective for the mutant BRAF sequence.

Figure 3:
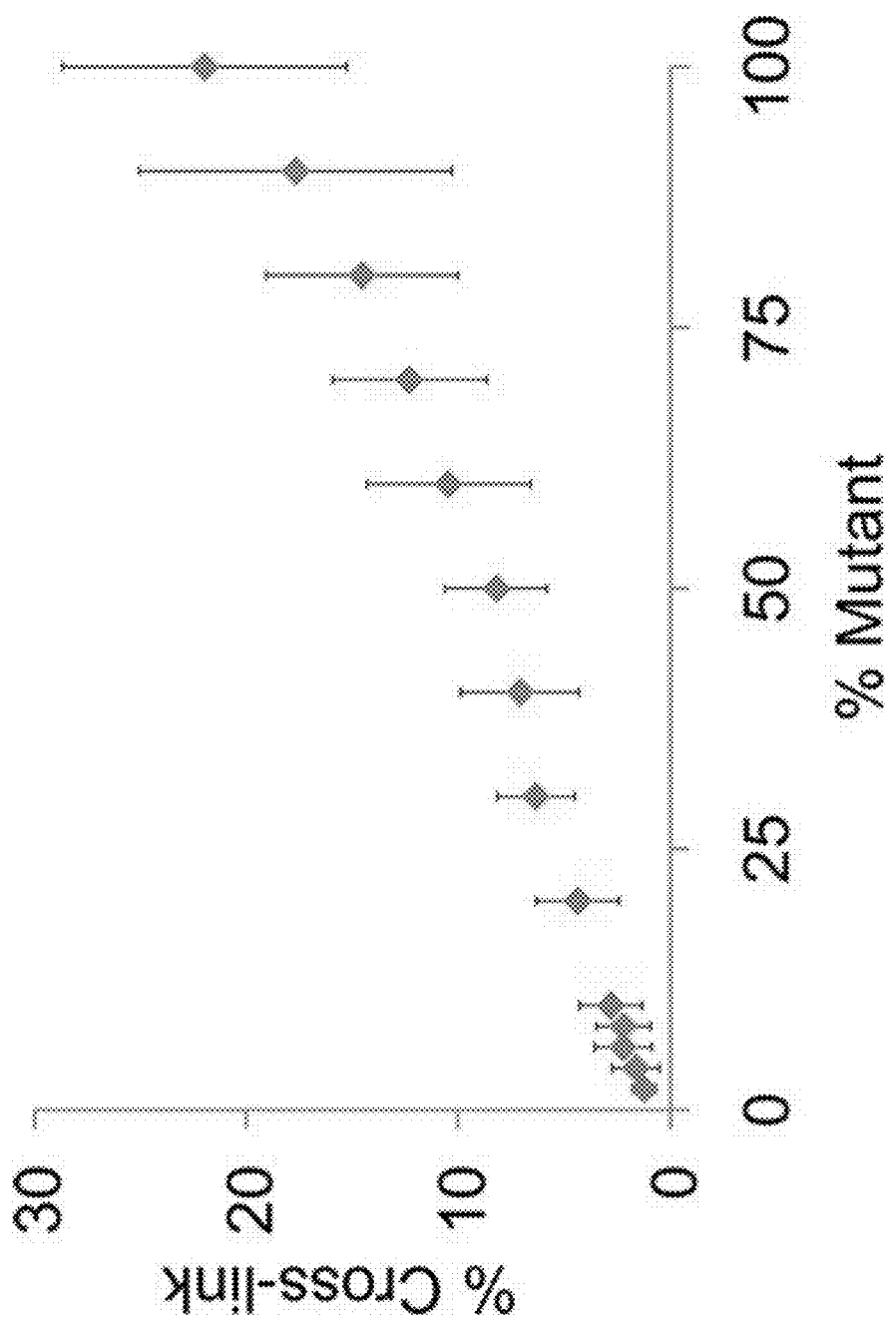

FIG. 3. FIG. 3 shows crosslink yield as a function of the amount of mutant BRAF sequence present in mixtures of mutant and wild-type duplexes. Samples run in triplicate containing various proportions of mutant and wild-type BRAF duplexes (21 bp) were denatured by warming at 70° C. in the presence of an Ap probe containing an adenine residue on the 3'-side of the Ap site, cooled, incubated at 37° C., and assessed by gel electrophoretic analysis to determine the yield of inter-strand crosslink.

Figure 4A:
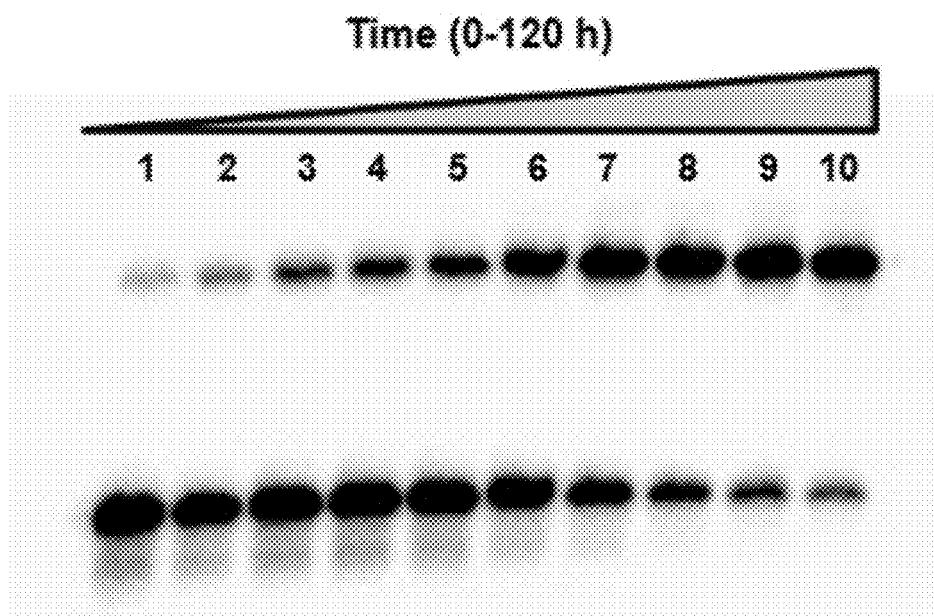

FIG. 4A,B. FIG. 4 shows the rate of crosslinked DNA generated from the mutant BRAF-probe over time. A) Gel electrophoretic analysis (denaturing 20% polyacrylamide gel) of crosslink formation in 21 bp duplexes containing an Ap-containing probe and the mutant BRAF sequence (top probe SEQ ID NO: 1; bottom Mutant BRAF SEQ ID NO: 2) after 0, 1, 3, 5, 7, 10, 24, 48, 72, 96, and 120 hour incubations. The lower bands correspond to the uncrosslinked 32P-labeled probes, and the upper bands cross-linked 32P-labeled duplexes of probe and mutant target DNA. B) Crosslinked duplexes of probe and mutant target DNA were quantitatively measured by phosphorimager analysis. For crosslinking reactions, Ap-containing duplexes were incubated in HEPES buffer (50 mM, pH 7 containing 100 mM NaCl) at 37° C. for the indicated time points.

Figure 5A:
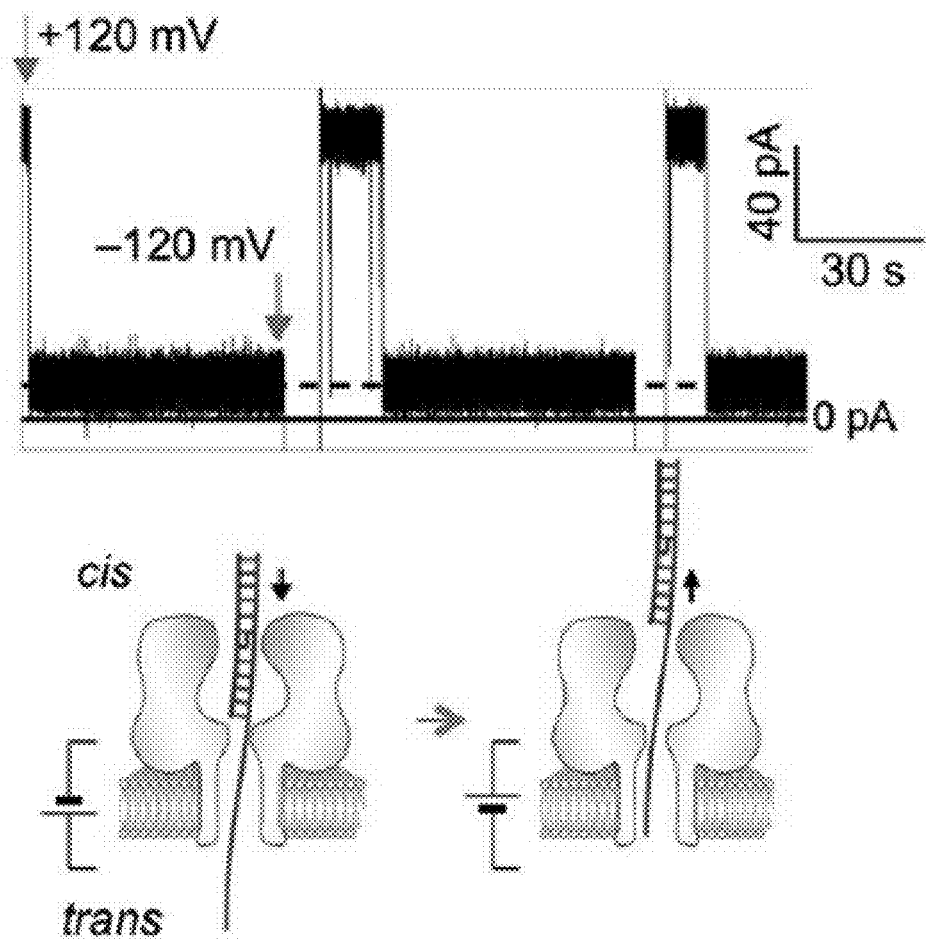

FIG. 5A,B. FIG. 5 shows crosslinked DNA generated from the mutant BRAF-probe duplex E can be readily detected by its unique current signature in the α-HL nanopore. The mixtures of species generated by incubation of a tagged probe with either mutant or wild-type BRAF gene sequences were analyzed by using a single α-HL ion channel embedded in a lipid bilayer. Current traces were recorded at +120 mV in Tris (10 mm, pH 7.4) containing KCl (1 M) at 22° C.: A) analysis of the mixture generated by hybridization of the mutant BRAF sequence with the Ap-containing probe strand. The current block was recorded for 1 min, then voltage polarity was reversed to translocate the crosslinked duplex back to the cis solution (top probe SEQ ID NO: 1; bottom Mutant BRAF SEQ ID NO: 2) and B) wild-type BRAF sequence does not generate crosslinked DNA when hybridized with the Ap-containing probe strand. Short current blocks are consistent with translocation of single-stranded DNA and uncrosslinked duplex F (top probe SEQ ID NO: 1; bottom Wild-type BRAF SEQ ID NO: 3). The illustration depicts the three-step unzipping/translocation process for duplex DNA.

Figure 6:
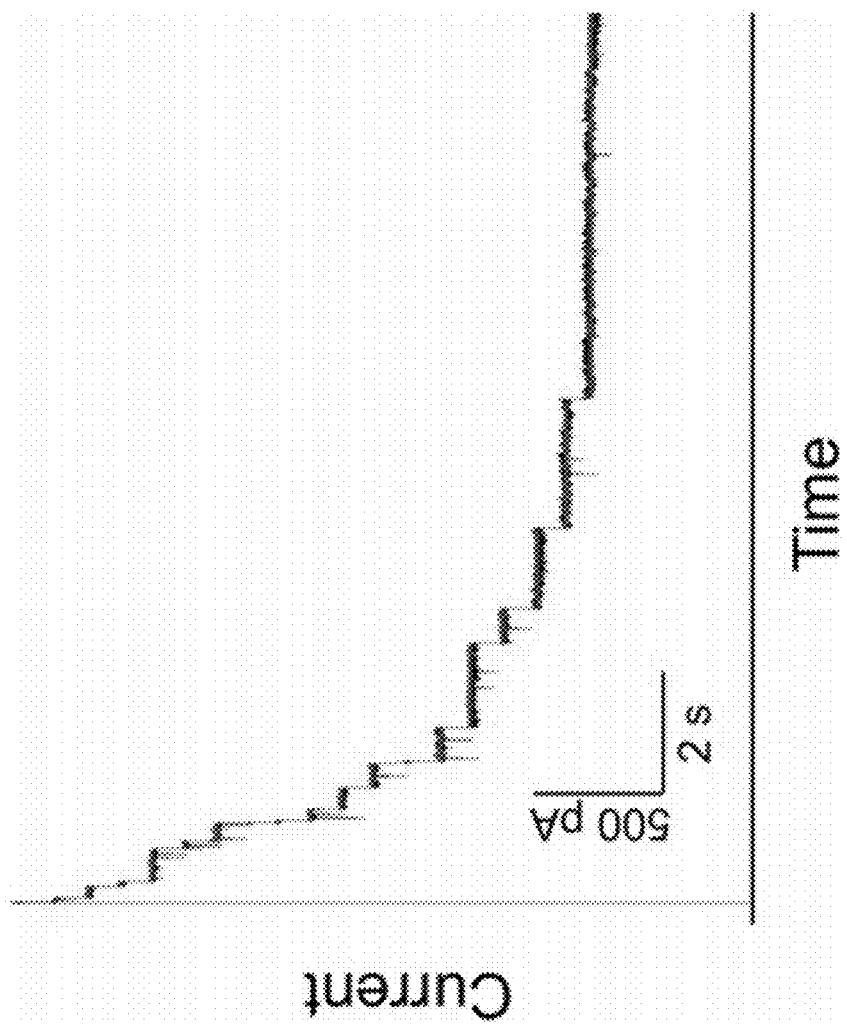

FIG. 6. FIG. 6 shows the incremental current decreases induced by sequential, irreversible blocking of individual α-HL pores by crosslinked duplexes in an experiment with multiple channels embedded in the lipid bilayer. The mixture contained crosslinked duplex, un-crosslinked duplex, and single strands. The analysis was carried out at 120 mV in Tris buffer (10 mm, pH 7.4) containing KCl (1 M) at 22° C. The trace shown was low-pass filtered at 1 kHz.

FIG. 7. FIG. 7 illustrates DNA duplexes (A-G) used in studies of FIGS. 8-15. A: top (probe) SEQ ID NO: 4; bottom (target) SEQ ID NO: 2. B: top SEQ ID NO: 4; bottom SEQ ID NO: 3. C: top SEQ ID NO: 5; bottom SEQ ID NO: 2. D: top SEQ ID NO: 5; bottom SEQ ID NO: 3. E: top SEQ ID NO: 1; bottom SEQ ID NO: 2. F: SEQ ID NO: 1. G: SEQ ID NO: 2.

FIG. 8A,B. FIG. 8 shows Ap-containing probes selectively cross-link with the 1799 T→A mutant BRAF kinase gene sequence: A) Gel electrophoretic analysis of cross-link formation between a first Ap-containing probe in a 21 nt duplex; and B) cross-linking by second Ap-probe that introduces a mismatch adjacent to the Ap residue. The middle bands correspond to the $^{32}$P-labeled full length labeled 2'-deoxyoligonucleotides and the upper bands cross-linked DNA. Ap sites were generated by treatment of the corresponding 2'-deoxyuridine-containing duplex with UDG. The Ap-containing duplexes were incubated in HEPES buffer (50 mM, pH 7 containing 100 mM NaCl) at 37° C. After 120 h, the loading dye was added to the reaction mixture for gel analysis. The $^{32}$P-labeled 2'-deoxyoligonucleotides were resolved on a denaturing 20% polyacrylamide gel and the radioactivity in each band was quantitatively measured by phosphorimager analysis. A) Lane 1 dU-containing duplex A, lane 2 Ap-containing duplex A, lanes 3 piperidine work up of duplex A, Lane 4 duplex A after 120 h incubation in the buffer, Lane 5 dU-containing duplex B, lane 6 Ap-containing duplex B, lanes 7 piperidine work up of duplex B, and Lane 8 duplex B after 120 h incubation in the buffer. B) Lane 1 dU-containing duplex C, lane 2 Ap-containing duplex C, lanes 3 Ap-containing duplex C, lane 4 piperidine work up of duplex C, Lane 5 duplex C after 120 h incubation in the buffer, Lane 5 dU-containing duplex D, lane 6 Ap-containing duplex D, lanes 7 piperidine work up of duplex D, and Lane 8 duplex D after 120 h incubation in the buffer.

FIG. 9A-E. FIG. 9 shows iron-EDTA footprinting defines the cross-link location in duplex E: A) Lane 1 is a Maxam-Gilbert G-lane of the labeled 2'-deoxyoligonucleotide strand in duplex E. Lane 2 is an A+G lane of the labeled 2'-deoxyoligonucleotide strand in duplex E. Lane 3 is the iron-EDTA cleavage reaction on the labeled 2'-deoxyoligonucleotide duplex E. Lane 4 is the iron-EDTA footprinting on the cross-linked duplex E. B), C) and D) are densitometry traces of lanes 1, 2 and 4 on the sequencing gel A) where each peak represents a band on the gel. E): top SEQ ID NO: 1; bottom SEQ ID NO: 2.

Figure 10:
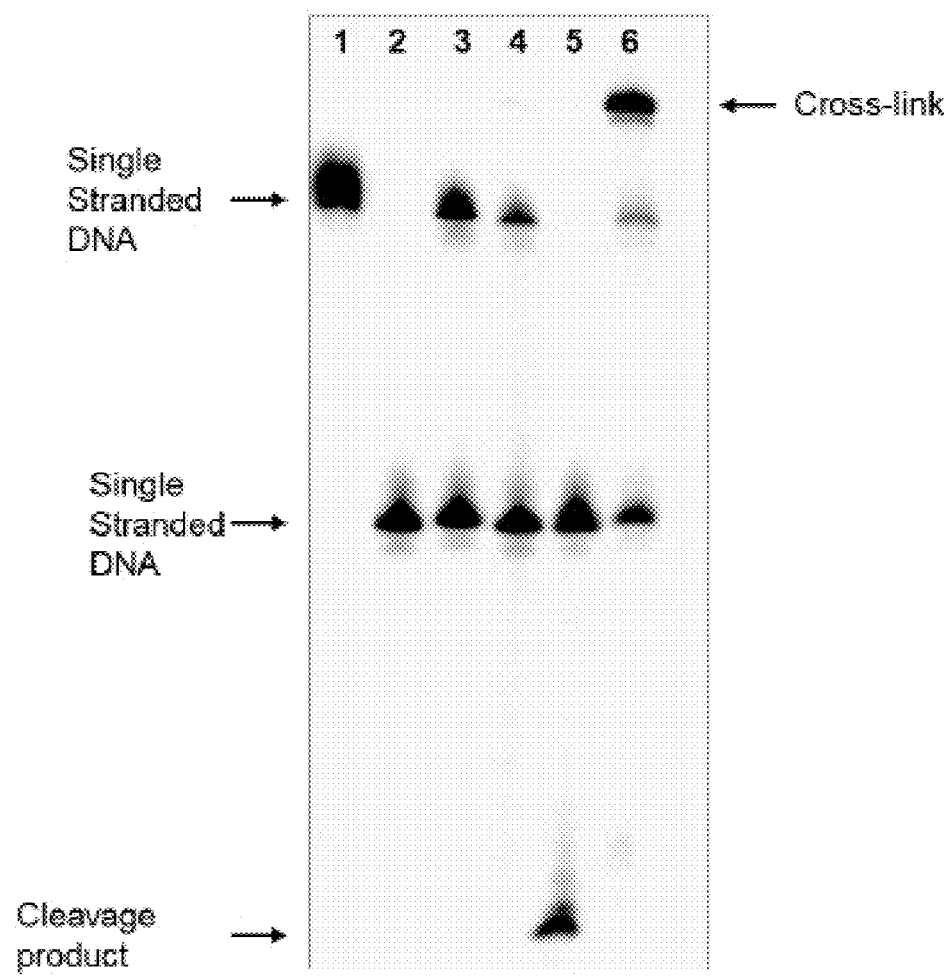

FIG. 10. FIG. 10 shows quantitative detection of cross-linked duplex E prepared for nanopore experiment by gel analysis. After generation of dA-Ap cross-link for nanopore experiment under standard condition, the DNA was radiolabeled and analyzed by gel electrophoresis. The radioactivity in each band was quantitatively measured by phosphorimager analysis. Lane 1 dU-containing strand F, Lane 2 strand G, lane 3 dU-containing duplex E, lane 4 Ap-containing duplex E, lane 5 piperidine work up of duplex E, and Lane 6 Ap-containing duplex E after 120 h incubation in HEPES buffer (50 mM, pH 7 containing 100 mM NaCl) at 37° C.

Figure 11A:
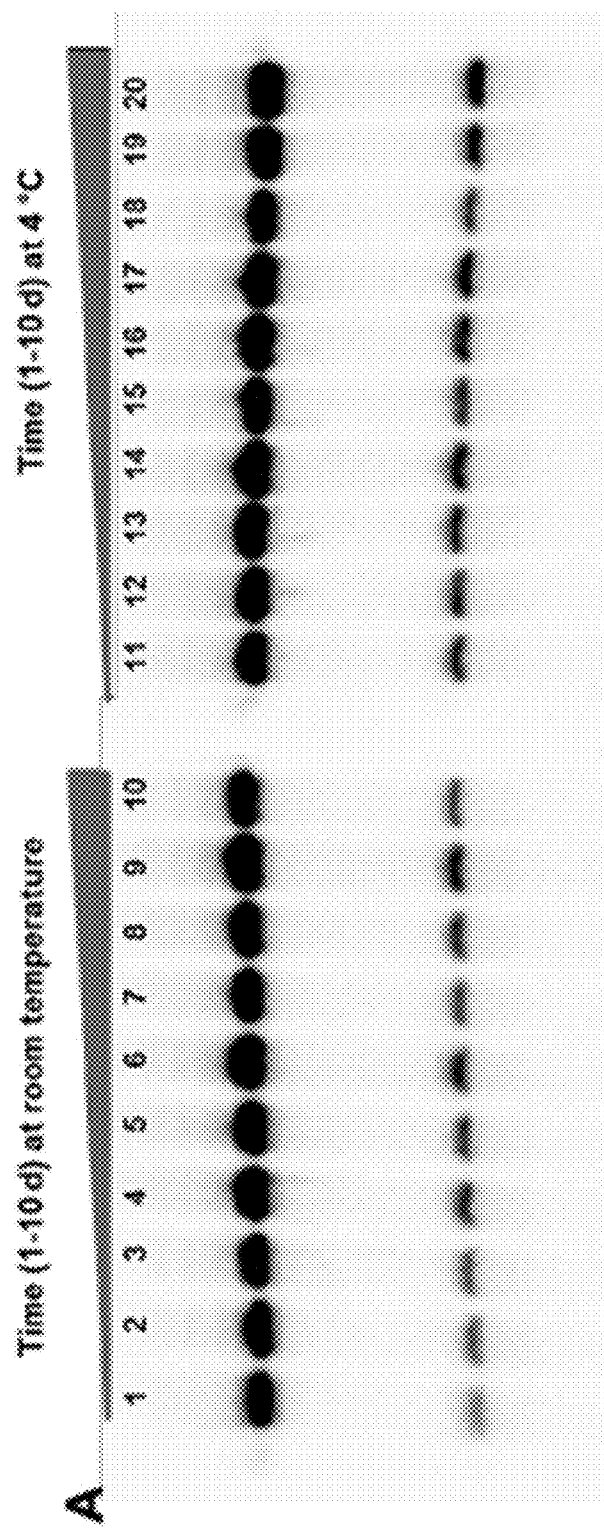
Figure 11B:
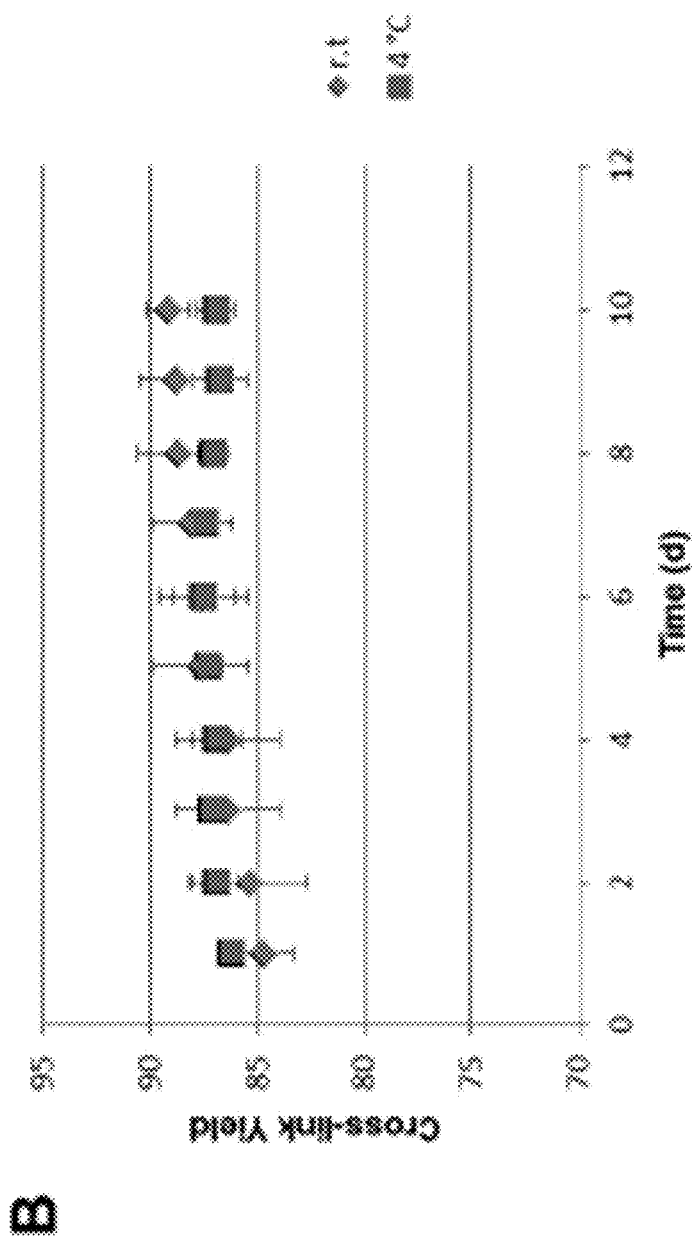

FIG. 11A,B. FIG. 11 shows the effect of storage condition on the cross-link yield. After the cross-link generation using standard procedure, the dA-Ap cross-link was stored in 2 different conditions, room temperature (r.t.) and 4° C. for 10 days. At specified time points, aliquots were removed and frozen at −20° C. before gel analysis. A) The $^{32}$P-labeled 2'-deoxyoligonucleotides were resolved on a denaturing 20% polyacrylamide gel and B) the radioactivity in each band was quantitatively measured by phosphorimager analysis.

Figure 12:
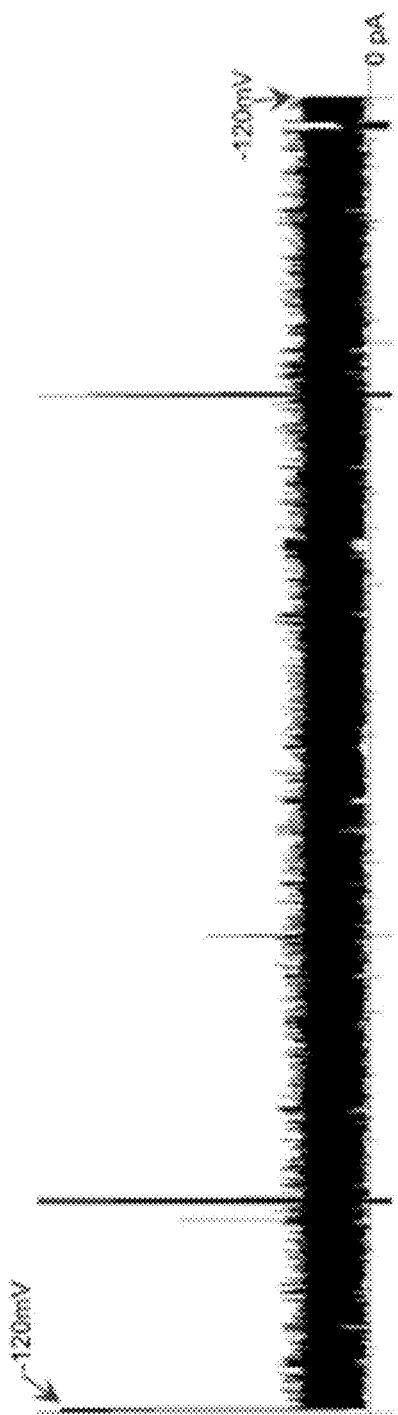

FIG. 12. FIG. 12 shows a continuous recording of the block by cross-linked mutant target/probe duplex E for 30 min at +120 mV, in 1 M KCl, 10 mM Tris, pH 7.4 at 22° C. The result demonstrates the permanent trapping and current blocking of the cross-linked DNA duplex in the nanopore.

Figure 13:
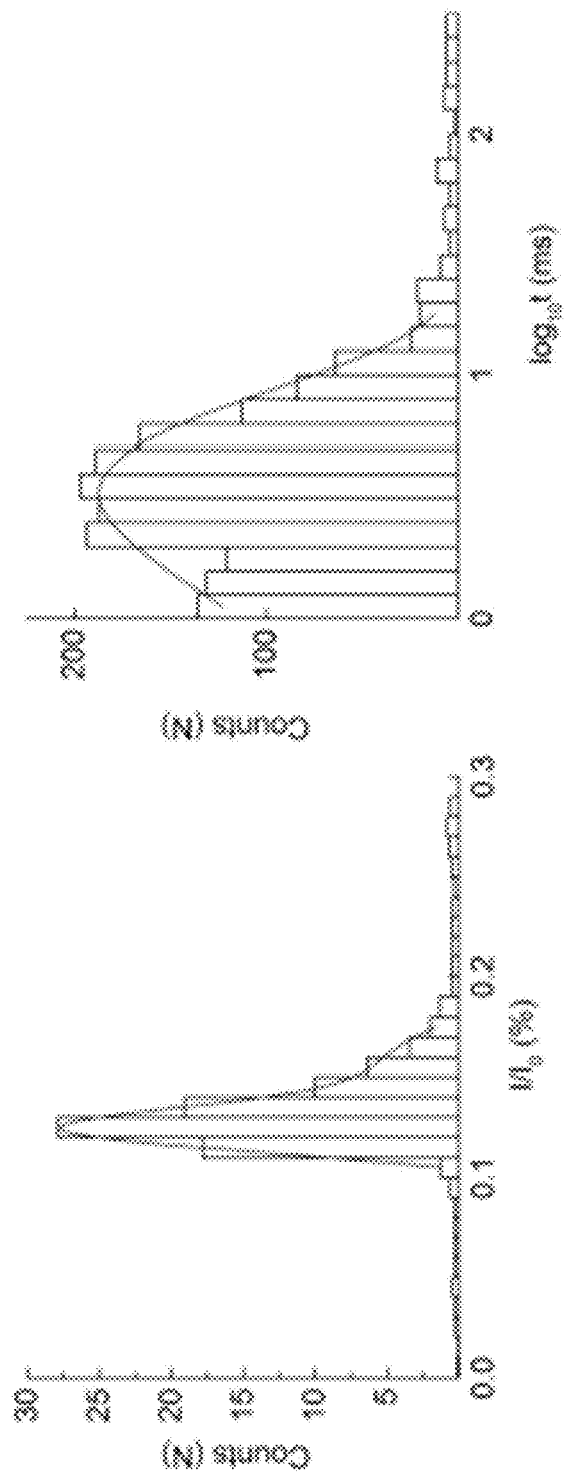

FIG. 13. FIG. 13 contains histograms showing the current-blocking levels (left) and dwell times (right) for the uncross-linked duplex F.

Figure 14:
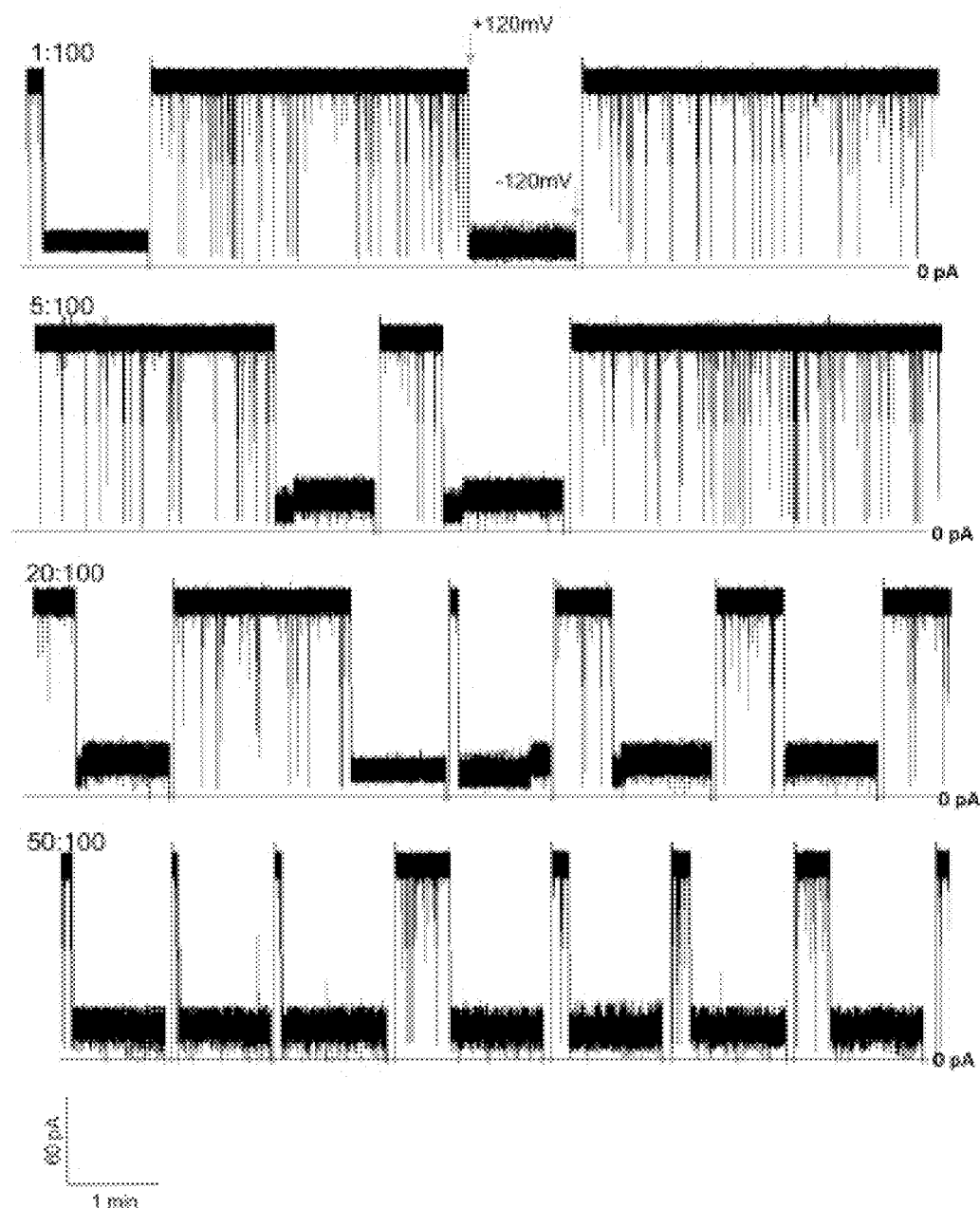

FIG. 14. FIG. 14 show current traces for mixtures of cross-linked duplex E and uncross-linked duplex F. These were single-channel experiments recorded at +120 mV, for 10 min in 1 M KCl, 10 mM Tris, pH 7.4 at 22° C. When irreversible trapping of a cross-linked duplex was recorded, the voltage polarity was reversed to −120 mV to clear the nanopore and then reset to +120 mV to resume sampling the nucleic acids in the mixture. Samples containing larger fractions of cross-linked duplex (lower traces) yield more frequent irreversible current blocks.

Figure 15:
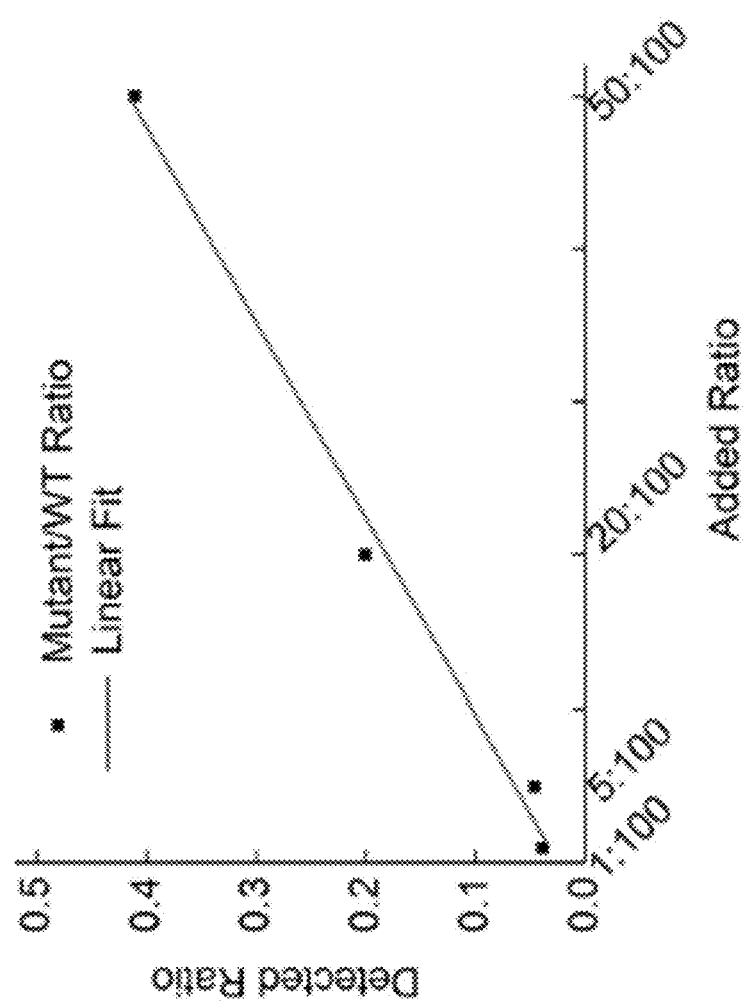

FIG. 15. FIG. 15 shows a plot of detected ratio of persistent current blocking events versus short-duration current blocks as a function of the ratio of cross-linked duplex E:uncross-linked duplex F in sample (based on data shown in FIG. 14).

DETAILED DESCRIPTION

Overview

Disclosed herein is a method of covalently crosslinking nucleic acid strands. In certain aspects, the method comprises incubating a hybridized, double-stranded DNA molecule (dsDNA), comprising a probe strand that comprises an abasic (Ap) residue and an at least partially complementary target strand that comprises a 2'-deoxyadenosine (dA) residue, under conditions that allow for a covalent crosslinking reaction to occur between the Ap residue in the probe strand and the dA residue in the target strand. In certain aspects, the Ap residue is at a position immediately 5' adjacent to the nucleotide residue in the probe strand that is directly opposite to the dA residue in the target strand.

The disclosed hybridization-induced, programmable crosslinking reaction can be used for the sequence specific covalent capture of nucleic acids. The probe-target complexes generated in this manner can be detected by many protocols, for example, by typical fluorescence (A. P. Silverman, et al., *Chem. Rev.* 2006, 106, 3775; J. G. Wetmur, *Crit. Rev. Biochem. Mol. Biol.,* 1991, 26, 227; S. Tyagi, et al., *Nat. Biotechnol.* 1996, 14, 303; A. P. Silverman, et al., *Adv. Clin. Chem.* 2007, 43, 79; V. V. Demidov, et al., *Trends Biochem. Sci.* 2004, 29, 62; L. Hu, et al., *Biomark. Res.* 2014, 2, 3), colorimetric (I. Alexandre, et al., *Anal. Biochem.* 2001, 295, 1), or electrochemical methods (X. Li, et al., *Anal. Chem.* 2006, 78, 6096). In certain aspects, nanopore technology, combined with sequence-specific crosslinking chemistry, provides a high contrast—in essence, digital—signal for single-molecule sensing of nucleic acid sequences.

The disclosure provides for crosslinking probes prepared in a one-step procedure from inexpensive commercial reagents. Such probes achieved excellent sequence specificity under isothermal assay conditions. In certain aspects, crosslinked nucleic acids, such as crosslinked DNA duplexes, disclosed herein can be quantitatively measured by using denaturing gel electrophoresis and/or a protein nanopore. As noted, in certain aspects, the crosslinking process of this disclosure involves the covalent reaction of an abasic (Ap) site in the probe strand with a 2'-deoxyadenosine (dA) residue in the target strand (FIG. 1A) (N. E. Price, et al., *Am. Chem. Soc.* 2014, 136, 3483-3490; N. E. Price, et al., *Nucleic Acids Res.* 2015, 43, 3434). The Ap-containing probe strands were easily generated by treatment of the corresponding 2'-deoxyuridine-containing oligodeoxyribonucleotide with the enzyme uracil DNA glycosylase (UDG) (N. E. Price, et al., *Am. Chem. Soc.* 2014, 136, 3483-3490; N. E. Price, et al., *Nucleic Acids Res.* 2015, 43, 3434; T. Lindahl, et al., *J. Biol. Chem.* 1977, 252, 3286; U. Varshney, et al., *Biochemistry* 1991, 30, 4055; J. Gamboa Varela, et al., *Angew. Chem. Int. Ed.* 2015, 54, 7666; *Angew. Chem.* 2015, 127, 7776; Z. Yang, et al., *Biochemistry* 2015, 54, 4259; M. J. Catalano, et al., *Bioorg. Med. Chem. Lett.* 2016, 26, 2627).

It was determined that in certain aspects, the dA-Ap crosslinking reaction can selectively detected a single-nucleotide polymorphism (SNP), such as in a human gene sequence (M. I. Nejad, et al., *ChemBioChem* 2017, 18, 1383-1386). SNPs are the smallest differences that can exist in nucleic acid sequences yet have immense importance in biology and medicine (E. S. Lander, *Nature* 2011, 470, 187; J. J. McCarthy, et al., *Sci. Transl. Med.* 2013, 5, 189sr4; P. E. M. Gibbs, C. W. Lawrence, *J. Mol. Biol.* 1995, 251, 229; K. M. Giacomini, et al., *Clin. Pharmacol. Ther.* 2007, 81, 328; K. Knez, et al., *Analyst* 2014, 139,353; S. H. Katsanis, et al., *Nat. Rev. Genet.* 2013, 14, 415; W. Shen, et al., *TrAC Trends Anal. Chem.* 2015, 69, 1; L. D. S. Lapitan, Jr., et al., *Analyst* 2015, 140, 3872). For example, a T→A mutation at position 1799 of the BRAF kinase gene sequence represents an oncogenic V600E substitution in the protein (J. C. Rubinstein, et al., *J. Transl. Med.* 2010, 8, 1; C. Sun, et al., *Nature* 2014, 508, 118; G. Bollag, et al., *Nat. Rev. Drug Discovery* 2012, 11, 873) and the anticancer drug vemurafenib (Zelboraf) specifically inhibits the V600E kinase (J. C. Rubinstein, et al., *J. Transl. Med.* 2010, 8, 1; C. Sun, et al., *Nature* 2014, 508, 118; G. Bollag, et al., *Nat. Rev. Drug Discovery* 2012, 11, 873).

Definitions

The terms defined immediately below are more fully defined by reference to the specification in its entirety. To the extent necessary to provide descriptive support, the subject matter and/or text of the appended claims is incorporated herein by reference in their entirety.

It will be understood by all readers of this written description that the exemplary aspects and embodiments described and claimed herein can be suitably practiced in the absence of any recited feature, element or step that is, or is not, specifically disclosed herein.

It is to be noted that the term "a" or "an" entity refers to one or more of that entity; for example, "a nucleic acid," is understood to represent one or more nucleic acids. As such, the terms "a" (or "an"), "one or more," and "at least one" can be used interchangeably herein.

Furthermore, "and/or" where used herein is to be taken as specific disclosure of each of the specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, technical and scientific terms used herein have the same meaning as commonly understood by one of ordinary skill in the art to which this disclosure is related. For example, unless otherwise specified, "complementary" base pairs refers to A/T and G/C base pairing.

Numeric ranges are inclusive of the numbers defining the range. Even when not explicitly identified by "and any range in between," or the like, where a list of values is recited, i.e., 1, 2, 3, or 4, the disclosure specifically includes any range in between the values, i.e., 1 to 3, 1 to 4, 2 to 4, etc.

The headings provided herein are solely for ease of reference and are not limitations of the various aspects or aspects of the disclosure, which can be had by reference to the specification as a whole.

As used herein, the term "identity," i.e., "percent identity" to an amino acid sequence or to a nucleotide sequence disclosed herein refers to a relationship between two or more nucleotide sequences or between two or more amino acid sequences. When a position in one sequence is occupied by the same nucleic acid base or amino acid in the corresponding position of the comparator sequence, the sequences are said to be "identical" at that position. The percentage "sequence identity" is calculated by determining the number of positions at which the identical nucleic acid base or amino acid occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window. In order to optimally align sequences for comparison, the portion of a nucleotide or amino acid sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using, i.e., the program "BLAST" which is available from the National Center for Biotechnology Information, and which program incorporates the programs BLASTN (for nucleotide sequence comparison) and BLASTP (for amino acid sequence comparison), which programs are based on the algorithm of Karlin and Altschul (Proc. Natl. Acad. Sci. USA 90(12):5873-5877, 1993).

The term "nucleic acid" is a well-known term of art and is used herein to include DNA and RNA. Unless otherwise specified, a "nucleic acid" molecule and "polynucleotide" can be used interchangeably. A nucleic acid can comprise a conventional phosphodiester bond or a non-conventional bond (i.e., an amide bond, such as found in peptide nucleic acids (PNA)). In certain aspects, a nucleic acid is DNA. By "isolated" nucleic acid it is intended a nucleic acid molecule that has been removed from its native environment, such as a sample of genomic DNA obtained from a subject. Isolated RNA molecules include in vivo or in vitro RNA transcripts of polynucleotides. Isolated polynucleotides or nucleic acids further include such molecules produced synthetically.

As used herein the term "engineered" includes manipulation of nucleic acid or polypeptide molecules by synthetic means (i.e. by recombinant techniques, in vitro peptide synthesis, by enzymatic or chemical coupling of peptides or some combination of these techniques).

Methods of Ap-Site Covalently Crosslinking

Certain aspects of this disclosure are directed to a method of covalently crosslinking nucleic acid strands. As generally referred to, the strands to be crosslinked are a target strand and a probe strand. While not limited by its origin, the target strand can be obtained, for example, from a subject for genetic testing, such as to detect a disease-associated mutation, or from an organism, such as a bacteria, virus, fungus, plant, or animal for genetic identification. By "obtained" from a subject it is meant that the target strand can be directly isolated from the subject or the target strand is derived from a nucleic acid molecule and/or nucleic acid sequence of the subject, such as by molecular cloning and/or amplification techniques, such that the target strand maintains the genetic information of the subject. In certain aspects, the method of covalently crosslinking the nucleic acid strands comprises incubating a hybridized, double-stranded nucleic acid molecule comprising (i) a probe strand that comprises an abasic (Ap) residue and (ii) an at least partially complementary target strand that comprises a 2'-deoxyadenosine (dA) residue (FIG. 1A, FIG. 1B, and FIG. 1C). In certain aspects, the nucleic acid of either or both of the probe strand and the target strand can be any nucleic acid including DNA, RNA, a modification of DNA or RNA, or any other synthetic nucleic acid, as long at the probe strand and the target strand nucleic acids are capable of specifically hybridizing to each other via complementary sequence. In certain aspects, the probe strand, the target strand, or both the probe strand and the target strand are DNA molecules. By "hybridized, double-stranded nucleic acid molecule," and "at least partially complementary" it is meant that the probe strand and the target strand are not necessarily complementary in sequence and/or hybridized along their entire lengths. The amount of complementarity and/or hybridization between the probe strand and the target strand need not be 100% but should be sufficient under the hybridization conditions to allow complementary hybridization at least of the sequence surrounding the Ap residue in the probe strand and the dA residue in the target strand. Positionally, the Ap residue in the probe strand is at a position immediately 5' adjacent to the nucleotide residue in the probe strand that is directly opposite to the dA residue in the target strand (FIG. 1B and FIG. 1C). Incubation occurs under conditions that allow for a covalent crosslinking reaction to occur between the Ap residue in the probe strand and the dA residue in the target strand (FIG. 1A). As discussed herein, the crosslinking reaction can occur under a wide variety of conditions, including for example a wide range of: temperature; solvent type; buffer type and/or concentration; reaction pH; reactant concentration; and/or time (FIG. 1A and FIG. 1B).

While the Ap residue in the probe strand is at a position immediately 5' adjacent to the nucleotide residue in the probe strand that is directly opposite to the dA residue in the target strand, the nucleotide residue in the probe strand that is actually directly opposite to the dA residue in the target strand can be any nucleotide residue. In certain aspects, the nucleotide residue in the probe strand that is directly opposite to the dA residue in the target strand can be, for example, 2'-deoxythymidine (dT), 2'-deoxyadenosine (dA), 2'-deoxycytosine (dC), or 2'-deoxyguanine (dG). In certain aspects, the nucleotide residue in the probe strand that is directly opposite to the dA residue in the target strand is dA.

Figure 4B:
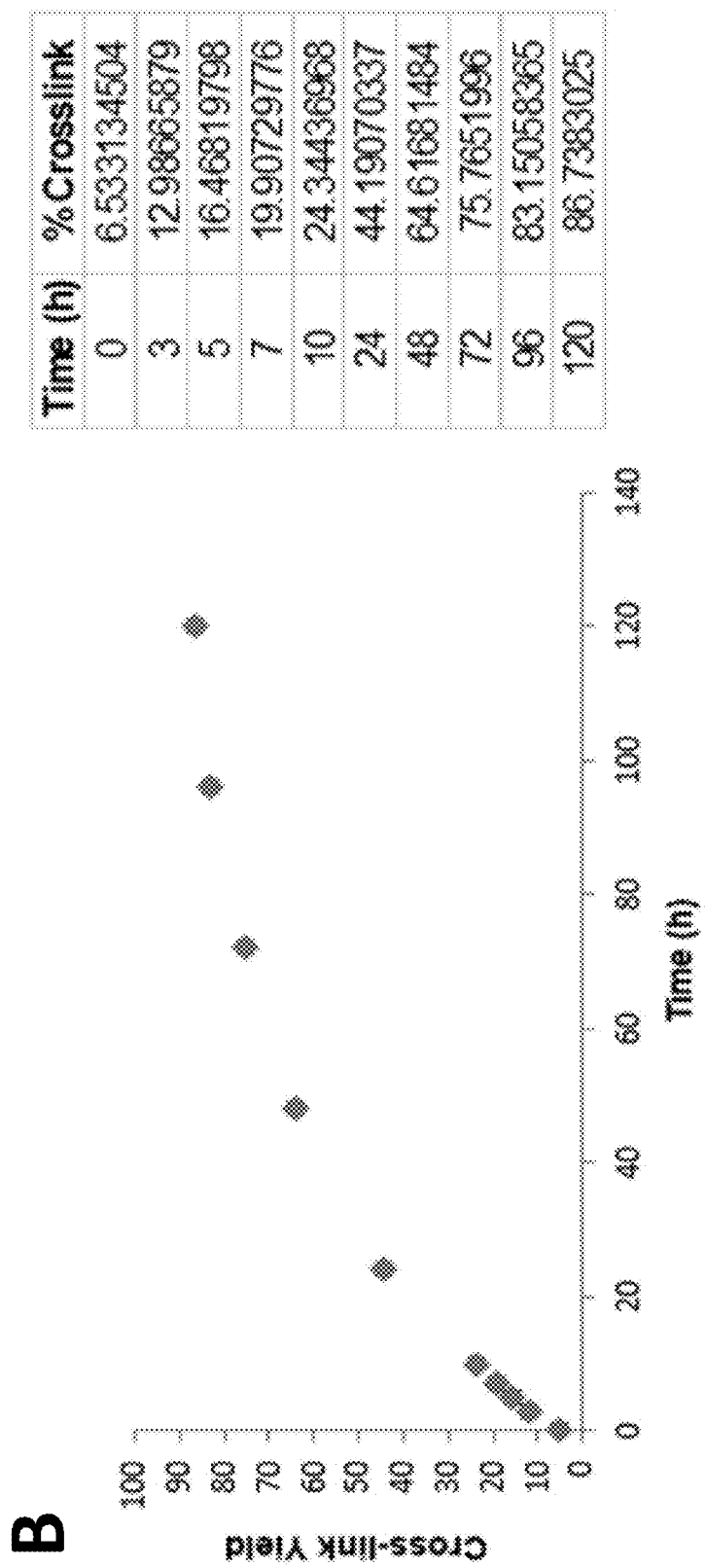

An advantage of the present disclosure is that the crosslinking reaction is isothermal, that is, no double-strand (i.e., dsDNA) melting is required and hence, the reaction outcome is not highly sensitive to conditions and temperature. N. E. Price, et al., *Am. Chem. Soc.* 2014, 136, 3483-3490. Therefore, in certain aspects, stringent control of reaction conditions is not required. In certain aspects, stringent control of reaction conditions is not required as long as the conditions allow for hybridization of the probe strand and target strand to form an at least partially hybridized double-stranded nucleic acid molecule. In certain aspects, the hybridized nucleic acid molecule is incubated at physiological pH. In certain aspects, the hybridized nucleic acid molecule is incubated in HEPES buffer. In certain aspects the hybridized nucleic acid molecule is incubated at or at about pH 7. In certain aspects the hybridized nucleic acid molecule is incubated at or at about 37° C. In certain aspects, incubation occurs in the presence of or of about 100 mM NaCl. In addition, in further non-limiting examples, representative incubation conditions can comprise one or more of: HEPES buffer (50 mM, pH 7; 100 mM NaCl); Cacodylate (50 mM, pH 7, 100 mM NaCl); NaH$_2$PO$_4$/citric acid (16.5/1.8 mM, pH 7.0, 100 mM NaCl); MOPS (50 mM, pH 7, 100 mM NaCl); Bis-Tris (50 mM, pH 7.4, 100 mM NaCl); and in the presence of the biological thiol glutathione (1 mM, in HEPES 50 mM, pH 7, 100 mM NaCl). Without being bound by theory, it is contemplated that longer incubation times will provide higher yields. In certain aspects, the incubation time is, or is about, or is at least or is at least about 1 hour, 2 hours, 3 hours, 4 hours, 5 hours, 6 hours, 9 hours, 12 hours, 15 hours, 18 hours, 24 hours, 36 hours, 48 hours, 96 hours, or 120 hours, or any range in between (FIG. 4A and FIG. 4B).

One of ordinary skill in the art would understand that at some point prior to incubating the hybridized double-stranded nucleic acid molecule to allow for the crosslinking reaction to occur between the Ap residue of the probe strand and the dA residue of the target strand, the probe strand and target strand are contacted to allow the probe strand and the target strand to hybridize to form the hybridized double-stranded nucleic acid molecule.

In certain aspects, the probe strand should be of sufficient length to contain a sequence of sufficient length to specifically hybridize to a complementary sequence on the target strand. In certain aspects, the length of the probe strand is limited to avoid non-specific binding. In certain aspects, the probe strand is less than or is less than about 100, 90, 80, 70, 60, 50, 40, 30, 29, 28, 27, 26, 25, 24, 23, 22, 21, 20, 19, 18, 17, 16, 15, 14, or 13 nucleotides in length. In certain aspects, the probe strand is or is about 100, 90, 80, 70, 60, 50, 40, 30, 29, 28, 27, 26, 25, 24, 23, 22, 21, 20, 19, 18, 17, 16, 15, 14, 13, or 12 nucleotides in length, or any range in-between. In certain aspects, the probe strand is not less than or is not less than about 20, 19, 18, 17, 16, 15, 14, 13, or 12 nucleotides in length. In certain aspects, the target strand should be of sufficient length to contain a sequence of sufficient length to specifically hybridize to a complementary sequence on the probe strand. In certain aspects, the target strand is at least or is at least about 12, 13, 14, 15, 16, 17, 18, 19, 20, 21, 22, 23, 24, 25, 26, 27, 28, 29, 30, 40, 50, 60, 70, 80, 90, or 100 nucleotides in length. In certain aspects, the target strand is or is about 12, 13, 14, 15, 16, 17, 18, 19, 20, 21, 22, 23, 24, 25, 26, 27, 28, 29, 30, 40, 50, 60, 70, 80, 90, or 100 nucleotides in length, or any range in between. In certain aspects, the hybridized nucleic acid molecule (i.e., dsDNA) comprises a hybridized portion containing the Ap residue of the probe strand (and thus the corresponding dA residue position for crosslinking in the target strand) that is at least or at least about 12, 13, 14, 15, 16, 17, 18, 19, 20, 21, 22, 23, 24, 25, 26, 27, 28, 29, 30, 40, 50, 60, 70, 80, 90, or 100 nucleotides in length. In certain aspects, the hybridized nucleic acid molecule (i.e., dsDNA) comprises a hybridized portion containing the Ap residue of the probe strand (and thus the corresponding dA residue position for crosslinking in the target strand) that is or is about 12, 13, 14, 15, 16, 17, 18, 19, 20, 21, 22, 23, 24, 25, 26, 27, 28, 29, 30, 40, 50, 60, 70, 80, 90, or 100 nucleotides in length, or any range in between. One of ordinary skill in the art will recognize that a hybridized portion of nucleic acid can contain one or more mismatched base pairs, including at the dA residue position, and still remain hybridized. In certain aspects, the hybridized portion containing the Ap residue of the probe strand is at least or is at least about 50%, 60%, 70%, 75%, 80%, 85%, 90%, 95%, 96%, 97%, 98%, or 99% complementary, excluding the position of the Ap residue. In certain aspects, the hybridized portion containing the Ap residue of the probe strand is or is about 50%, 60%, 70%, 75%, 80%, 85%, 90%, 95%, 96%, 97%, 98%, 99%, or 100% complementary, or any range in between, excluding the position of the Ap residue.

In certain aspects, the crosslinking reaction between the Ap and dA residues of the probe strand and target strand, respectively, forms a covalent crosslink. Without being bound by theory, one of ordinary skill in the art would recognize that a covalent bond is generally more stable than the hydrogen bonding between complementary nucleic acid base pairs. Thus, in certain aspects, the covalent crosslinking increases stability of the double-stranded nucleic acid molecule (i.e., dsDNA) in comparison to a hybridized double-stranded molecule with identical strand sequences but that is not crosslinked. The increase in stability resultant from the crosslinking reaction can be utilized to detect a dA residue in a target strand. In certain aspects, a probe strand and target strand are covalently crosslinking via the dA residue in the target strand and the Ap residue in a probe strand according to any method disclosed herein. The presence of crosslinking of the target and probe strands can then be detected by detecting an increase in the stability. In certain aspects, the increase in stability of the crosslinked nucleic acid molecule is compared against the stability of a hybridized double-stranded molecule with identical strand sequences but that is not crosslinked. In certain aspects, the presence of covalently crosslinking is detected by, for example, gel electrophoresis, monitoring of thermal stability, fluorescence methods (i.e. FRET), or a nanopore-based sensor. Further, it is contemplated that any method used to detect hybridization of uncross-linked probes could also be adapted for use to detect the cross-linked probe as well. Illustrative examples include microarrays, electrochemical detection, etc. When carried out at higher temperatures, these methods would melt-off uncross-linked duplexes, leaving only the cross-linked probe target complexes to be detected.

In certain aspects, the covalently crosslinking is detected by a nanopore-based sensor and results in increased signal, decreased background, and/or causes a permanent current block when the crosslinked nucleic acid molecule is subjected to an applied voltage in the nanopore-based sensor. U.S. Pat. Nos. 9,395,353, 9,574,228, 9,732,379, and International PCT Publications WO/2012/009578 and WO/2014/144217, which are incorporated by reference herein in their entireties; and Nakane et al., *Biophysical Journal* Volume 87, July 2004 615-621; Aksimentiev et al., *Biophysical Journal* Volume 88 June 2005 3745-3761; Maglia et al., *PNAS* Dec. 16, 2008, vol. 105, no. 50, pp. 19720-19725; Sanchez-Quesada et al., *Angew. Chem. Int. Ed.* 2004, 43, 3063-3067; and Howorka et al., *PNAS* Nov. 6, 2001 vol. 98, no. 23, pp. 12996-13001.

In certain aspects, the probe sequence is attached, immobilized, or the like on a polymer, scaffold, solid support (such as a resin or beads), and/or the like such that the crosslinking of the target strand to the probe strand "captures" the target strand. In certain aspects, non-crosslinking target strands can washed or otherwise removed from the crosslinked nucleic acids thereby concentrating and/or purifying target strands comprising the dA residue recognized by the Ap site.

Detection of the Presence or Absence of a dA Residue in a Target Strand

Provided herein is a method for detecting the presence or absence of a dA residue at a particular position in a nucleic acid strand. In certain aspects, the method comprises incubating a hybridized double-stranded nucleic acid molecule comprising (i) a probe strand that comprises an abasic (Ap) residue and (ii) an at least partially complementary target strand. The Ap residue of the probe strand is at a position that is immediately 5' adjacent to the nucleotide residue in the probe strand that is directly opposite to the particular position in the target strand where the presence or absence of the dA residue is to be detected. The incubation occurs under conditions, as described herein, that allow for a covalent crosslinking reaction to occur between the Ap residue in the probe strand and the dA residue in the target strand, if present. Certain aspects comprise detecting whether crosslinking of the target strand and probe strands occurred. The detection (or non-detection) of the crosslinking of the target strand and probe strand can be performed by any appropriate method including those disclosed anywhere herein. In certain aspects, the nucleic acid of the target strand, the probe strand, or the target and probe strand, is DNA. In certain aspects, the hybridized double-stranded nucleic acid molecule comprises dsDNA. In certain aspects, a dA residue is present at the particular position in the target strand and a covalent crosslinking reaction occurs between the Ap residue in the probe strand and the dA residue in the target strand. Thus, in certain aspects, the method is a method of detecting the presence of a dA residue in a nucleic acid strand.

In certain aspects, covalently crosslinking of the probe strand and the target strand, or the absence of crosslinking, is detected by, for example, gel electrophoresis, monitoring of thermal stability, fluorescence methods (i.e. FRET), or a nanopore-based sensor. Further, it is contemplated that any method used to detect hybridization of uncross-linked probes could also be adapted for use to detect the cross-linked probe as well. Illustrative examples include microarrays, electrochemical detection, etc. In certain aspects, the covalently crosslinking is detected by a nanopore-based sensor and results in increased signal, decreased background, and/or causes a permanent current block when the crosslinked nucleic acid molecule is subjected to an applied voltage in the nanopore-based sensor.

Detection of Mutations

Certain aspects provide for detecting a mutation in a wild-type sequence by detecting the presence or absence of a dA residue at a particular position in a target strand according to the methods disclosed herein. In certain aspects, the target strand is obtained from a sample taken from a subject for which genetic interrogation is desired. The sample can be for example, a blood draw, tissue biopsy, saliva, etc. Methods of isolating nucleic acids from a biological sample are well-known to those of ordinary skill in the art. A subject can be any animal such as a fish, bird, reptile, mammal, or marsupial. The subject can be a human. A subject can be a non-animal such as a plant, fungus, algae, virus, or bacteria. In certain aspects, where the dA residue is present at the particular position in the target strand, the mutation comprises a T→A, C→A, or G→A mutation. In certain aspects, where the dA residue is absent at the particular position in the target strand, the mutation comprises an A→T, A→C, or A→G mutation. One of ordinary skill in the art will recognize that because DNA is complementary and double-stranded, the characterization of, for example, a T→A or A→T, can depend on which strand (i.e., coding or non-coding strand) is used as the target strand. In certain aspects, the mutation is a single nucleotide polymorphism (SNP).

Without being bound by theory, it was suspected that flexibility introduced by mismatching of base pairs could enable crosslink formation between the Ap site in the target strand and the directly opposing residue in the target strand when a dA residue at the position to be interrogated is not present. This could result in false-positive crosslinking. Accordingly, in certain aspects, the probe strand sequence is complementary to the wild-type sequence at the position directly opposing the residue in the target strand be interrogated. Thus, in certain aspects where the mutation comprises a T→A, C→A, or G→A mutation, the nucleotide residue in the probe strand that is at the position immediately 5' adjacent to the Ap residue in the probe strand is complementary to the wild-type sequence of the target strand. For example, if the wild-type sequence contains a T (such that a target strand representing the wild-type sequence would contain a T at the position where the mutated sequence would contain A), the position immediately 5' adjacent to the Ap residue in the probe strand is A. Likewise, if the wild-type sequence contains a C (such that a target strand representing the wild-type sequence would contain a C at the position where the mutated sequence would contain A), the position immediately 5' adjacent to the Ap residue in the probe strand is G, and if the wild-type sequence contains a G (such that a target strand representing the wild-type sequence would contain a G at the position where the mutated sequence would contain A), the position immediately 5' adjacent to the Ap residue in the probe strand is C.

In certain aspects, the presence or absence of the dA residue in the target strand represents a disease relevant mutation. Thus, in certain aspects, the presence or absence of the dA residue in the target strand can be used to aid in a medical diagnosis. In certain aspects, the disease is cancer. In certain aspects, the cancer is BRAF-mutant ($BRAF^{Mut}$) colorectal cancer (CRC). In certain aspects, the presence or absence of a dA residue in the target strand is used to determine the potential resistance to treatment and/or best treatment options for the disease, cancer, tumor, etc.

Classification

Certain aspects also provide for classifying or identifying an organism by detecting the presence or absence of a dA residue at a particular position in a target strand according to the methods disclosed herein. The organism can be any of the subjects identified herein. For example, in certain aspects, a target strand is obtained from a sample taken from a bacteria, virus, or fungus, and the presence or absence of a dA residue in the target strand is used to identify the species, subspecies, or strain. In certain aspects, a target strand is obtained from a pathogen or suspected pathogen. In certain aspects, the presence or absence of a dA residue in the target strand is used to determine the virulence, potential resistance to treatment, and/or best treatment options for a pathogen and/or infection.

Crosslinked Nucleic Acids

Certain aspects of this disclosure provide for isolated covalently crosslinked, double-stranded nucleic acid molecules, comprising a probe strand that comprises an abasic (Ap) residue and an target strand that comprises a 2'-deoxyadenosine (dA) residue, wherein the Ap residue is at a position immediately 5' adjacent to the nucleotide residue in the probe strand that is directly opposite to the dA residue in the target strand, and wherein the Ap residue is covalently crosslinked to the dA residue in the target strand that is directly opposite to the nucleotide residue in the probe strand that is immediately 3' adjacent to the Ap residue. In certain aspects, the probe strand, the target strand, or both the probe strand and the target strand, is a DNA molecule. In certain aspects, the nucleotide residue in the probe strand that is immediately 3' adjacent to the Ap residue is dA, dT, dG, or dC. In certain aspects, the nucleotide residue in the probe strand that is immediately 3' adjacent to the Ap residue is dA.

In order to aid in the detection of crosslinking, the probe strand and/or the target strand can comprise a tag. For example, in certain aspects, the tag can be a fluorescent label. For example, in certain aspects, the probe strand and/or the target strand comprises a terminal extension that is covalently attached to the 5' end, the 3' end, or both the 5' end and the 3' end of the strand. In certain aspects, the terminal extension is selected from the group consisting of $poly(dC)_{(3-33)}$, $poly(dG)_{(3-33)}$, $poly(dA)_{(3-33)}$, $poly(dT)_{(3-33)}$, and $poly(dN)_{(3-33)}$, where N is any combination of 2'-deoxycytosine, 2'-deoxyguanosine, 2'-deoxyadenosine, thymine, an abase, inosine, xanthosine, 7-methylguanosine, dihydrouridine, or 5-methylcytidine. In certain aspects, the terminal extension is covalently attached to the 3' end of the probe strand and or the target strand. In certain aspects, the terminal extension is attached to the probe strand. In addition to polydA, polydT, polydG, and polydC, the terminal extension sequence could be a combination of all four bases, RNA, or RN/RNA co-polymers. The sequence can also be a DNA/RNA intermediate with a polymer spacer such as polyethylene glycol, or a polypeptide. Overall, there are many choices for terminal extensions.

Examples

An Ap-containing oligonucleotide probe was designed to crosslink with A1799 in the mutant BRAF sequence (FIG. 1C). Formation of the dA-Ap crosslink was previously observed (N. E. Price, et al., *Am. Chem. Soc.* 2014, 136, 3483-3490; N. E. Price, et al., *Nucleic Acids Res.* 2015, 43, 3434) when an adenine residue was positioned 1 nt to the 3'-side of the Ap site on the opposing strand (FIG. 1B), however, the sequence specificity of this crosslinking reaction was not characterized. Incubation of the mutant BRAF target-probe duplex A in HEPES buffer (50 mm, pH 7) containing NaCl (100 mm) at 37° C. gave a 7.3±2.0% yield of a slowly migrating band on a denaturing polyacrylamide gel, consistent with that expected (N. E. Price, et al., *Am. Chem. Soc.* 2014, 136, 3483-3490; N. E. Price, et al., *Nucleic Acids Res.* 2015, 43, 3434) for the crosslinked duplex (FIG. 2A, lane 1, and FIG. 8). In contrast, the wild-type target-probe duplex B gave a relatively low yield of a slowly migrating band (2.3±0.6%; FIG. 2A, lane 5).

A second-generation Ap-containing probe was designed to decrease the background signal associated with crosslinking to the wildtype BRAF sequence. The exact location of the crosslink generated between the first-generation probe and the wild-type sequence was uncertain, but it was suspected that flexibility introduced by the T-T mispair (G. Rossetti, et al., *Nucleic Acids Res.* 2015, 43, 4309) enabled crosslink formation between the Ap site and the directly opposing guanine residue (K. M. Johnson, et al., *J. Am. Chem. Soc.* 2013, 135, 1015; M. J. Catalano, et al. *J. Am. Chem. Soc.* 2015, 137, 3933; S. Dutta, et al., *J. Am. Chem. Soc.* 2007, 129, 1852). Accordingly, a new probe strand was prepared containing an adenine residue on the 3'-side of the Ap site, such that the probe was complementary to the wild-type BRAF sequence (duplex D, FIG. 2B). The background crosslink formation between the second-generation probe and the wild-type BRAF sequence in duplex D decreased to undetectable levels (FIG. 2B, lane 5). Further, the crosslink formation between the second-generation probe and the mutant BRAF target sequence in duplex C increased dramatically to 85±3% (FIG. 2B, lane 1 and FIG. 8). Iron-EDTA footprinting experiments confirmed that crosslink attachment in duplex C was to crosslink yield and the fraction of mutant duplex in the samples was observed (FIG. 3).

An α-hemolysin (α-HL) protein nanopore for single-molecule detection of the crosslinked probe-target duplex was examined. The α-HL ion channel can be used to create a device in which a nanoscale pore (1.4 nm wide) (L. Song, et al., *Science* 1996, 274, 1859) spans a lipid bilayer that separates two chambers of aqueous electrolyte (W. Shi, et al., *Anal. Chem.* 2017, 89, 157; B. M. Venkatesan, et al., *Nat. Biotechnol.* 2011, 6, 615; M. Wanunu, *Phys. Life Rev.* 2012, 9, 125). Application of an electric potential induces a readily measured ion current, and the sequence and structure of nucleic acids can be analyzed based upon the characteristic current blocks produced when they are driven into the pore by the electrophoretic potential (R. P. Johnson, et al., *J. Am. Chem. Soc.* 2017, 139, 2750; Y. S. Ang, et al., *ACS Nano* 2012, 6, 8815; Q. Zhao, et al., *Nano Lett.* 2007, 7, 1680; S. M. Iqbal, et al., *Nat. Nanotechnol.* 2007, 2, 243; J. Kong, et al., *Chem. Commun.* 2017, 53, 436; X. Zhang, et al., *J. Am. Chem. Soc.* 2015, 137, 15742; Y. Wang, et al., *Nat. Nanotechnol.* 2011, 6, 668; K. Tian, et al., *ACS Nano* 2017, 11, 1204). For the nanopore experiments, a third-generation Ap-containing probe strand was prepared with a $dC_{30}$ overhang on the 3'-end (FIG. 4 and FIG. 5). A poly-dC extension was employed to increase the rate at which the α-HL nanopore captures the duplexes and to facilitate rapid unzipping of (un-crosslinked) duplexes in the nanopore (R. P. Johnson, et al., *J. Am. Chem. Soc.* 2017, 139, 2750; Y. S. Ang, et al., *ACS Nano* 2012, 6, 8815; Q. Zhao, et al., *Nano Lett.* 2007, 7, 1680; S. M. Iqbal, et al., *Nat. Nanotechnol.* 2007, 2, 243; J. Kong, et al., *Chem. Commun.* 2017, 53, 436; X. Zhang, et al., *J. Am. Chem. Soc.* 2015, 137, 15742; Y. Wang, et al., *Nat. Nanotechnol.* 2011, 6, 668; K. Tian, et al., *ACS Nano* 2017, 11, 1204; X. Zhang, et al., *ACS Nano* 2015, 9, 11812). Separate gel electrophoretic analysis demonstrated that crosslink yields were not affected by the $dC_{30}$ overhang (FIG. 10 and FIG. 11).

In a device employing a single α-HL nanopore embedded in the lipid bilayer, analysis of the mixture generated by combination of the Ap probe with the mutant BRAF target sequence (duplex E) revealed several distinct current signatures. For example, very short current blocks were observed, consistent with the translocation of single strands ($I/I_0$=13.2±0.3%; τ=150±30 μs) and un-crosslinked duplexes ($I/I_0$=12.2±0.9%; T=12±0.3 ms; FIG. 5) (W. Shi, et al., *Anal. Chem.* 2017, 89, 157; B. M. Venkatesan, et al., *Nat. Biotechnol.* 2011, 6, 615; M. Wanunu, *Phys. Life Rev.* 2012, 9, 125). Persistent current blocks ($I/I_0$=13.2±0.3%, FIG. 5A) were observed, consistent with capture of a crosslinked duplex in the nanopore. Following capture of the crosslinked duplex, current flow could be restored only when the voltage polarity of the nanopore device was reversed; this caused the crosslinked duplex to back out of the channel.

Figure 5B:
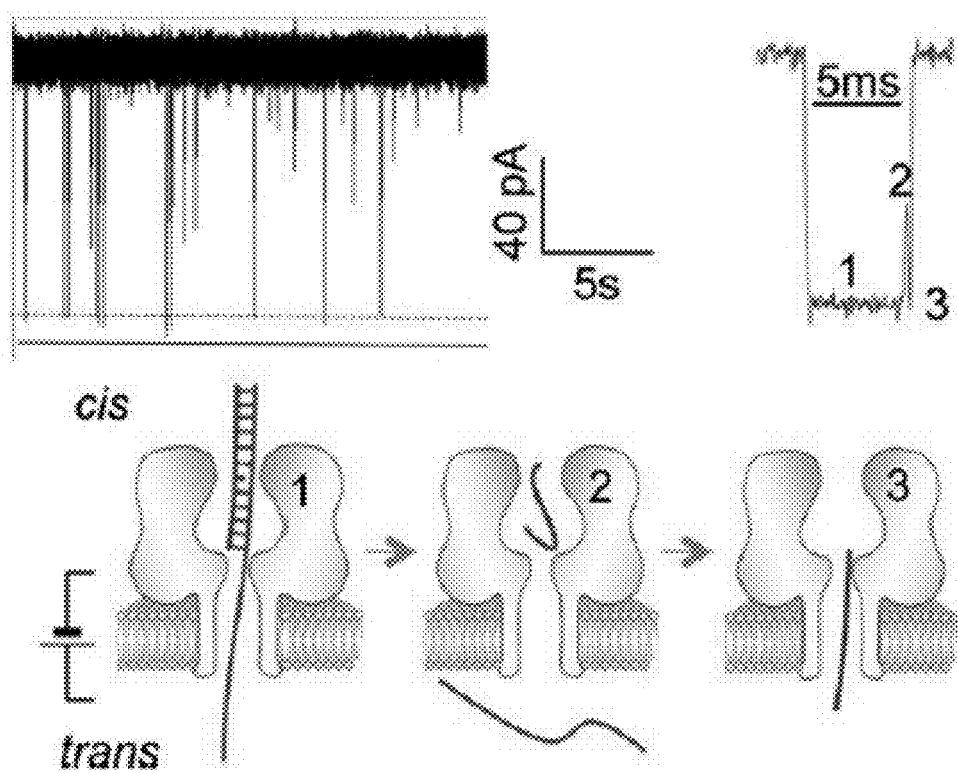

When the voltage polarity was reset, the open pore was again able to record current signatures associated with the nucleic acid species in the bulk mixture (FIG. 5A). Analysis of the mixture generated by combination of the Ap probe with the wild-type BRAF gene sequence (duplex F) revealed no persistent current blocks, only short current blocks consistent with the translocation of single strands and un-crosslinked duplexes (FIG. 5B and FIG. 13). The current signature of a crosslinked duplex is unmistakably different from that of the un-crosslinked DNA, thus providing a high-contrast signal for detection of the BRAF mutation. When multiple α-HL ion channels were embedded in the lipid bilayer, the analysis of mixtures derived from mutant duplex E revealed a series of incremental current decreases consistent with sequential, irreversible blocking of individual pores by the crosslinked duplex (FIG. 6) (X. Zhang, et al., *ACS Nano* 2015, 9, 11812). By counting the number of events with each type of current signature, the nanopore could be used for the quantitative analysis of mixtures containing both mutant and wild-type BRAF sequences (FIG. 14 and FIG. 15).

Experimental Procedures

Materials and General Procedures.

Reagents were purchased from the following suppliers and were of the highest purity available: oligonucleotides were purchased from Integrated DNA Technologies (Coralville, Iowa). Uracil DNA glycosylase (UDG), and T4 DNA polynucleotide kinase (T4 PNK) were from New England Biolabs (Ipswich, Mass.). [γ-32P]-ATP (6000 Ci/mmol) was purchased from PerkinElmer. C-18 Sep-Pak cartridges were purchased from Waters (Milford, Mass.), and BS Poly prep columns were obtained from BioRad (Hercules, Calif.). Acrylamide/bis-acrylamide 19:1 (40% Solution/Electrophoresis) was purchased from Fisher Scientific (Waltham, Mass.). Quantification of radioactivity in polyacrylamide gels was carried out using a Personal Molecular Imager (BIORAD) with Quantity One software (v.4.6.5).

Preparation of Cross-Linked DNA Substrates.

The complementary oligonucleotides for each duplex were annealed (Deininger, P., et al., *Molecular cloning: A laboratory manual:* 2nd ed. Cold Spring Harbor Laboratory Press, Cold Spring Harbor, N.Y., 1989) at a 1:1 molar ratio and treated with the enzyme UDG (50 units/mL, final concentration) to generate Ap sites. The enzyme UDG was removed by phenol-chloroform extraction and the DNA ethanol precipitated and the pellet washed with 80% EtOH-water (Deininger, P., et al., *Molecular cloning: A laboratory manual:* 2nd ed. Cold Spring Harbor Laboratory Press, Cold Spring Harbor, N.Y., 1989). The resulting Ap-containing DNA duplexes were redissolved in a buffer composed of HEPES (50 mM, pH 7) containing NaCl (100 mM) and incubated at 37° C. for 120 h. Reaction mixtures were then analyzed in the nanopore experiments. In some cases, parallel denaturing polyacrylamide gel electrophoretic analysis of the cross-linking reaction mixture was carried out as previously described (Catalano, M. J. et al. *J Am Chem Soc*

2015, 137, 3933; Price, N. E.; et al., *J Am Chem Soc* 2014, 136, 3483). Briefly, the DNA was ethanol precipitated and 5'-$^{32}$P-labeled using standard procedures. After $^{32}$P-labeling, the protein was removed by phenol-chloroform extraction and the sample was desalted by passage through SEPHADEX G-25. The samples were then mixed with formamide loading buffer, loaded into the wells of a 20% denaturing polyacrylamide gel, and gel electrophoresed for 4 h at 1600 V. The amount of radiolabeled DNA in each band from the gel was measured by phosphorimager analysis. In these experiments, 0.5% yields of cross-linked DNA are easily detectable. This provides a discrimination factor of >160 for the probe shown in FIG. 2B (cross-link yield target/cross-link yield non-target).

Hydroxyl Radical Footprinting of the dA-Ap Cross-Linked Duplex.

Art known protocols were employed to footprint cross-link duplex E (Sczepanski, J. T.; et al., *J Am Chem Soc* 2009, 131, 11132); (Luce, R. A.; et al., *Methods in enzymology* 2001, 340, 396). In this experiment, the strand opposing the Ap-containing oligonucleotide was 5'-labeled using standard procedure (Deininger, P., et al., *Molecular cloning: A laboratory manual:* 2nd ed. Cold Spring Harbor Laboratory Press, Cold Spring Harbor, N.Y., 1989). Labeled DNA was annealed with the uracil-containing complement and treated with UDG to generate the abasic site as described above. The Ap-containing double-stranded DNA (~400,000 cpm) was incubated in HEPES buffer (50 mM, pH 7) containing NaCl (100 mM) at 37° C. for 120 h. The DNA was ethanol precipitated, suspended in formamide loading buffer and separated on a 2 mm thick 20% denaturing polyacrylamide gel. The slow-forming cross-link duplex band was visualized using X-ray film, the band cut out of the gel, and the gel slice crushed, and the gel pieces were vortexed in elution buffer (NaCl, 200 mM; EDTA, 1 mM) at room temperature for at least 1 h. The mixture was filtered through a Poly-Prep column to remove gel fragments, and the residue was ethanol precipitated and redissolved in water and diluted with 2× oxidation buffer (10 µL of a solution composed of sodium phosphate, 20 mM, pH 7.2; NaCl, 20 mM sodium ascorbate, 2 mM; $H_2O_2$, 1 mM). To this mixture was added a solution of iron-EDTA (2 EDTA, 70 mM; $(NH_4)_2Fe(SO_4)_2 \cdot 6H_2O$, 70 mM) to start the reaction, and the mixture vortexed briefly and incubated at room temperature for 5 min before addition of thiourea stop solution (10 µL of a 100 mM solution in water). Hydroxyl radical footprinting reactions, Maxam-Gilbert G reactions, and Maxam-Gilbert A+G reactions were performed on the labeled duplex to generate marker lanes (Maxam, A. M.; et al., *Methods in enzymology* 1980, 65, 499). The resulting DNA fragments were analyzed using gel electrophoresis as described above.

Electrophysiology Measurements.

A membrane of 1,2-diphytanoyl-sn-glycero-3-phosphocholine was formed on a small orifice of approximately 150 µm diameter in a Teflon partition that separates two identical Teflon chambers. Each chamber contained 2 mL of electrolyte solution (1 M KCl, 10 mM Tris-HCl, pH 7.4). Less than 1 µL of α-hemolysin was added to the cis chamber with stirring, after which, a conductance increase indicated the formation of a single channel. For multichannel recording, 2 to 5 µL of α-hemolysin was added. The ionic current through the α-hemolysin protein nanopore was recorded by an Axopatch 200B amplifier (Molecular Devices Inc., Sunnyvale, Calif.), filtered with a built-in 4-pole low-pass Bessel Filter at 5 kHz, and finally acquired into the computer using a DigiData 1440A A/D converter (Molecular Devices) at a sampling rate of 20 kHz. All the data recording and acquisition including single channel, multichannel and persistent blocking recording of DNA cross-links were controlled through a Clampex program (Molecular Devices) and the analysis of nanopore current traces was performed using Clampfit software 10.4 (Molecular Devices).

The breadth and scope of the present disclosure should not be limited by any of the above-described exemplary aspects and embodiments, but should be defined only in accordance with the following claims and their equivalents.

What is claimed is:

1. A method of covalently crosslinking nucleic acid strands, the method comprising incubating a hybridized, double-stranded nucleic acid molecule, comprising (i) a probe strand that comprises an abasic (Ap) residue and (ii) an at least partially complementary target strand that comprises a 2'-deoxyadenosine (dA) residue, wherein incubation occurs under conditions that allow for a covalent crosslinking reaction to occur between the Ap residue in the probe strand and the dA residue in the target strand, wherein the Ap residue is at a position immediately 5' adjacent to the nucleotide residue in the probe strand that is directly opposite of the dA residue in the target strand and wherein the nucleotide residue in the probe strand that is directly opposite of the dA residue in the target strand is dA.

2. The method of claim 1, wherein the probe strand, the target strand, or both the probe strand and the target strand, is a DNA molecule.

3. The method of claim 1, wherein:
 (i) the probe strand is between about 12 and 100 nucleotides in length;
 (ii) the target strand is at least about 12 nucleotides in length; and/or
 (iii) the hybridized, double-stranded nucleic acid molecule comprises a hybridized portion containing the Ap residue of the probe strand that is between about 12 and 100 contiguous nucleotides in length.

4. The method of claim 3, wherein the hybridized portion containing the Ap residue of the probe strand is at least 90% complementary, excluding the position of the Ap residue.

5. The method of claim 1, wherein the crosslinking increases stability of the double-stranded nucleic acid molecule in comparison to a hybridized nucleic acid molecule with identical probe strand and target strand sequences but that is not crosslinked.

6. A method of detecting the presence or absence of a dA residue at a particular position in a DNA target strand, the method comprising incubating a hybridized double-stranded DNA molecule (dsDNA) comprising (i) a probe strand that comprises an abasic (Ap) residue immediately 5' adjacent to a dA residue and (ii) an at least partially complementary target strand, wherein the Ap residue of the probe strand is at a position that is immediately 5' adjacent to the nucleotide residue in the probe strand that is directly opposite to the particular position in the target strand where the presence or absence of the dA residue is to be detected, wherein the incubation occurs under conditions that allow for a covalent crosslinking reaction to occur between the Ap residue in the probe strand and the dA residue in the target strand, if present, and detecting whether crosslinking of the target and probe strands occurred, thereby detecting the presence or absence of a dA residue at the particular position in the target strand.

7. The method of claim 6, wherein a dA residue is present at the particular position in the target strand and a covalent crosslinking reaction occurs between the Ap residue in the probe strand and the dA residue in the target strand, and wherein the method detects the presence of the dA residue in the target strand.

8. The method of claim 6, wherein covalently crosslinking of the probe strand and the target strand is detected by gel electrophoresis, monitoring of thermal stability, fluorescence methods, electrochemistry, surface plasmon resonance, or a nanopore-based sensor.

9. The method of claim 8, wherein covalently crosslinking of the probe strand and the target strand is detected by a nanopore-based sensor.

10. A method of detecting a mutation of a wild-type sequence, the method comprising detecting the presence or absence of a dA residue at a particular position in a target strand according to the method of claim 6.

11. The method of claim 10, wherein the dA residue is present at the particular position in the target strand and the mutation comprises a T→A, C→A, or G→A mutation or the dA residue is absent at the particular position in the target strand and the mutation comprises an A→T, A→C, or A→G mutation.

12. The method of claim 11, wherein the mutation comprises a T→A, C→A, or G→A mutation and the nucleotide residue in the probe strand that is at the position immediately 5' adjacent to the Ap residue in the probe strand is complementary to the wild-type sequence of the target strand.

13. The method of claim 10, wherein the presence or absence of the dA residue represents a disease relevant mutation.

14. The method of claim 13, wherein the disease is cancer.

* * * * *